(12) United States Patent
Lerchner et al.

(10) Patent No.: US 8,008,250 B2
(45) Date of Patent: Aug. 30, 2011

(54) MACROCYCLIC COMPOUNDS AND COMPOSITIONS USEFUL AS BACE INHIBITORS

(75) Inventors: Andreas Lerchner, Binningen (CH); Rainer Machauer, Freiburg (DE); Marina Tintelnot-Blomley, Maulburg (DE); Oliver Simic, Basel (CH)

(73) Assignee: Novartis AG, Basel (CH)

( * ) Notice: Subject to any disclaimer, the term of this patent is extended or adjusted under 35 U.S.C. 154(b) by 293 days.

(21) Appl. No.: 11/794,412

(22) PCT Filed: Jan. 13, 2006

(86) PCT No.: PCT/EP2006/000265
§ 371 (c)(1),
(2), (4) Date: Jun. 26, 2007

(87) PCT Pub. No.: WO2006/074940
PCT Pub. Date: Jul. 20, 2006

(65) Prior Publication Data
US 2008/0214526 A1 Sep. 4, 2008

(30) Foreign Application Priority Data

Jan. 13, 2005 (GB) .................................. 0500683.8

(51) Int. Cl.
*A61K 31/551* (2006.01)
*C07D 243/00* (2006.01)
*C07K 7/50* (2006.01)

(52) U.S. Cl. ....... 514/2.9; 514/17.7; 514/17.8; 540/567; 530/317

(58) Field of Classification Search .......................... None
See application file for complete search history.

(56) References Cited

U.S. PATENT DOCUMENTS

| | | | |
|---|---|---|---|
| 6,969,709 B2 | 11/2005 | Pulley et al. | |
| 2003/0236199 A1* | 12/2003 | Pulley et al. | ............. 514/19 |
| 2007/0072792 A1 | 3/2007 | Auberson et al. | |
| 2008/0132477 A1 | 6/2008 | Betschart et al. | |
| 2009/0029960 A1 | 1/2009 | Betschart et al. | |
| 2009/0170878 A1 | 7/2009 | Machauer | |
| 2009/0312370 A1 | 12/2009 | Laumen et al. | |
| 2010/0022500 A1 | 1/2010 | Auberson et al. | |

FOREIGN PATENT DOCUMENTS

| | | |
|---|---|---|
| EP | 0 675 122 A2 | 10/1995 |
| WO | WO 92/18490 A1 | 10/1992 |
| WO | 02/100399 | 12/2002 |
| WO | 02/100856 | 12/2002 |
| WO | WO 2004/062625 A2 | 7/2004 |
| WO | 2005/003106 | 1/2005 |
| WO | 2005/016876 | 2/2005 |
| WO | WO 2005/018545 A2 | 3/2005 |
| WO | 2005/049585 | 6/2005 |
| WO | 2006/014944 | 2/2006 |
| WO | WO 2006/074940 A2 | 7/2006 |
| WO | WO 2006/074950 A1 | 7/2006 |
| WO | WO 2007/077004 A1 | 7/2007 |

OTHER PUBLICATIONS

Auberson, U.S. PTO Notice of Allowance, U.S. Appl. No. 10/577,260, Jun. 22, 2009, 8 pgs.
Auberson, U.S. PTO Office Action, U.S. Appl. No. 10/577,260, Feb. 27, 2008, 10 pgs.
Auberson, U.S. PTO Office Action, U.S. Appl. No. 10/577,260, Sep. 30, 2008, 14 pgs.
Betschart, U.S. PTO Office Action, U.S. Appl. No. 11/794,413, Feb. 4, 2010, 5 pgs.
Betschart, U.S. PTO Office Action, U.S. Appl. No. 11/794,413, Jul. 20, 2010, 16 pgs.
Betschart, U.S. PTO Office Action, U.S. Appl. No. 12/159,742, Sep. 8, 2010, 7 pgs.
Betschart, U.S. PTO Office Action, U.S. Appl. No. 12/159,742, Nov. 22, 2010, 12 pgs.
Chemical Abstracts No. 118:81414 (1992), 2 pgs.
Ripka et al., "Synthesis of Novel Cyclic Protease Inhibitors using Grubbs Olefin Metathesis", Bioorganic & Medicinal Chemistry Letters, vol. 8 (1998), pp. 357-360.
Smith et al., "Design, Synthesis, and Activity of Conformationally-Constrained Macrocyclic Peptide-Based Inhibitors of Huv Protease", Bioorganic & Medicinal Chemistry Letters, vol. 4, No. 18 (1994), pp. 2217-2222.
Hardy, "A Hundred Years of Alzheimer's Disease Research", Neuron, vol. 52 (2006), pp. 3-13.
Auberson, U.S. PTO Office Action, U.S. Appl. No. 12/566,928, Mar. 29, 2011, 14 pgs.
Betschart, U.S. PTO Notice of Allowance, U.S. Appl. No. 12/159,742, Mar. 29, 2011, 12 pgs.
Laumen, U.S. PTO Office Action, U.S. Appl. No. 12/374,467, Mar. 29, 2011, 13 pgs.
Laumen, U.S. PTO Restriction Requirement, U.S. Appl. No. 12/374,467, Jan. 25, 2011, 6 pgs.
Auberson, U.S. PTO Restriction Requirement, U.S. Appl. No. 12/566,928, Jan. 5, 2011, 7 pgs.
Betschart, U.S. PTO Notice of Allowance, U.S. Appl. No. 11/794,413, Jan. 18, 2011, 6 pgs.
Machauer, U.S. PTO Restriction Requirement, U.S. Appl. No. 12/374,469, Jun. 22, 2011, 5 pgs.

* cited by examiner

*Primary Examiner* — Julie Ha
(74) *Attorney, Agent, or Firm* — Paul D. Strain; Strain & Strain PLLC

(57) ABSTRACT

Macrocyclic compounds of the formula in which $R_1$, $R_3$, $V_1$, $V_2$, $X_1$, $X_2$, Y, Z, Ar, AA and n are as defined in the specification, the number of ring atoms included in the macrocyclic ring being 14, 15, 16, 17 or 18, in free base form or in acid addition salt form, to their preparation, to their use as medicaments and to medicaments comprising them are presented.

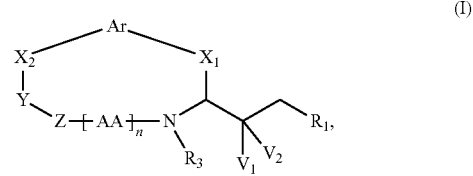

(I)

8 Claims, No Drawings

MACROCYCLIC COMPOUNDS AND COMPOSITIONS USEFUL AS BACE INHIBITORS

SEQUENCE LISTING

The instant application contains a Sequence Listing which has been submitted via EFS-Web and is hereby incorporated by reference in its entirety. Said ASCII copy, created on Mar. 17, 2010, is named 093286-0118-SequenceListing.txt and is 655 bytes in size.

The present invention relates to novel macrocyclic compounds, to their preparation, to their use as medicaments and to medicaments comprising them.

More particularly the invention relates to a compound of the formula

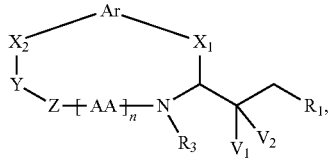

(I)

in which
$R_1$ is $(CH_2)_k N(R_a)R_b$, in which
k is 0, 1 or 2; and either
$R_a$ and $R_b$, independently, are hydrogen or an optionally substituted $(C_{1-8})$alkyl, $(C_{3-7})$cycloalkyl, $(C_{3-7})$cycloalkyl$(C_{1-4})$alkyl, aryl, aryl$(C_{1-4})$alkyl, heteroaryl, heteroaryl-$(C_{1-4})$alkyl, chroman-4-yl, isochroman-4-yl, thiochroman-4-yl, isothiochroman-4-yl, 1,1-dioxo-1lambda*6*-thiochroman-4-yl, 2,2-dioxo-2lambda*6*-isothiochroman-4-yl, 1,2,3,4-tetrahydroquinol-4-yl, 1,2,3,4-tetrahydroisoquinol-4-yl, 1,2,3,4-tetrahydronaphth-1-yl, 1,1-dioxo-1,2,3,4-tetrahydro-1lambda*6*-benzo[e][1,2]thiazin-4-yl, 2,2-dioxo-1,2,3,4-tetrahydro-2lambda*6*-benzo[c][1,2]thiazin-4-yl, 1,1-dioxo-3,4-dihydro-1H-1lambda*6*-benzo[c][1,2]oxathiin-4-yl, 2,2-dioxo-3,4-dihydro-2H-2lambda*6*-benzo[e][1,2]oxathiin-4-yl, 2,3,4,5-tetrahydrobenzo[b]oxepin-5-yl or 1,3,4,5-tetrahydrobenzo[c]oxepin-5-yl group or
$R_a$ and $R_b$, together with the nitrogen, to which they are attached, form an optionally substituted pyrrolidinyl, 1-piperidinyl, 4-morpholinyl or piperazinyl group;
$R_3$ is hydrogen or $(C_{1-4})$alkyl; either
$V_1$ is hydrogen and
$V_2$ is hydroxy or
$V_1$ and $V_2$ together are oxo;
$X_1$ is $(C_{1-8})$alkylene;
$X_2$ is $(C_{1-8})$alkylene, O, S, C(=O), C(=O)O, OC(=O), C(=O)N(R_2)—$(C_{1-8})$alkylenoxy attached via its carbonyl function to Y and attached via the oxygen atom of its alkylenoxy moiety to Ar, $N(R_2)C(=O)$, $C(=O)N(R_2)$ or $N(R_2)$, in which
$R_2$ is hydrogen or $(C_{1-4})$alkyl;
Y is $(C_{1-10})$alkylene, $(C_{1-8})$alkylenoxy$(C_{1-6})$alkylene, $(C_{1-10})$alkenylene or $(C_{1-8})$alkenylenoxy-$(C_{1-6})$alkylene;
Ar is phenylene optionally mono-, di- or tri-substituted by, independently, hydroxy or halogen, to which $X_1$ and $X_2$ are attached in meta or para position to each other; and either
Z is C(=O),
AA is a natural or non-natural alpha-amino acid residue attached via the nitrogen atom of its alpha-amino moiety to Z and attached via the carbonyl function of its acid moiety to the nitrogen atom of the amino moiety carrying $R_3$ (the hydroxy group of the carboxy moiety of the alpha-amino acid being replaced by the amino moiety carrying $R_3$) and
n is 0 or 1 or
Z is $S(=O)_2$,
AA is an optionally substituted 1,2-ethylenecarbonyl group (derived from a natural or non-natural alpha-amino acid by replacement of the alpha-amino moiety with a methylene group and by deletion of the hydroxy group of the carboxy moiety of the alpha-amino acid) attached via the methylene group in beta-position to its carbonyl function to Z and attached via its carbonyl function to the nitrogen atom of the amino moiety carrying $R_3$ and
n is 1,
the number of ring atoms included in the macrocyclic ring being 14, 15, 16, 17 or 18, in free base form or in acid addition salt form.

On account of the asymmetrical carbon atoms present in the compounds of the formula I, the compounds may exist in pure optically active form or in the form of mixtures of optical isomers, e. g. in the form of racemic mixtures. All pure optical isomers and their mixtures, including the racemic mixtures, are part of the present invention.

Halogen denotes fluorine, bromine, chlorine or iodine.

Optional substituents on alkyl or cycloalkyl groups or moieties or, when $R_a$ and $R_b$, together with the nitrogen, to which they are attached, form a substituted pyrrolidinyl, 1-piperidinyl, 4-morpholinyl or piperazinyl group, on the last mentioned substituted groups, may be one to four groups independently selected from hydroxy, hydroxy$(C_{1-4})$alkyl, $(C_{1-4})$alkoxy, $(C_{1-4})$-alkoxy$(C_{1-4})$alkyl, $(C_{1-4})$alkoxy$(C_{1-4})$alkoxy, $(C_{1-4})$alkylsulfanyl, $(C_{1-4})$alkoxycarbonyl, $(C_{1-4})$-alkylcarbonyloxy, $(C_{1-4})$alkylcarbonyl, $(C_{1-4})$alkylsulfonyl, cyano, oxo, $(C_{3-7})$cycloalkyl, optionally substituted aryl, optionally substituted aryl$(C_{1-4})$alkyl, optionally substituted heteroaryl and optionally substituted heteroaryl$(C_{1-4})$alkyl.

Optional substituents on chroman-4-yl, isochroman-4-yl, thiochroman-4-yl, isothiochroman-4-yl, 1,1-dioxo-1lambda*6*-thiochroman-4-yl, 2,2-dioxo-2lambda*6*-isothiochroman-4-yl, 1,2,3,4-tetrahydroquinol-4-yl, 1,2,3,4-tetrahydroisoquinol-4-yl, 1,2,3,4-tetrahydronaphth-1-yl, 1,1-dioxo-1,2,3,4-tetrahydro-1lambda*6*-benzo[e][1,2]thiazin-4-yl, 2,2-dioxo-1,2,3,4-tetrahydro-2lambda*6*-benzo[c][1,2]thiazin-4-yl, 1,1-dioxo-3,4-dihydro-1H-1lambda*6*-benzo[c]-[1,2]oxathiin-4-yl, 2,2-dioxo-3,4-dihydro-2H-2lambda*6*-benzo[e][1,2]oxathiin-4-yl, 2,3,4,5-tetrahydrobenzo[b]oxepin-5-yl, 1,3,4,5-tetrahydrobenzo[c]oxepin-5-yl, aryl or heteroaryl groups or moieties may be one to four, especially one to three, groups independently selected from hydroxy, $(C_{1-8})$alkyl, $(C_{1-6})$alkoxy, $S(=O)_2(C_{1-4})$alkyl, $(C_{3-7})$cycloalkyl, $(C_{3-7})$cycloalkyl-$(C_{1-4})$alkyl, cyano, nitro, trifluoromethyl, halogen, optionally substituted aryl, optionally substituted heteroaryl and optionally substituted carbamoyl.

When $R_a$ and/or $R_b$ is substituted aryl or heteroaryl, substituents may further be one to three groups selected from benzyloxy, phenoxy, $S(=O)_2NH_2$, $N(H)S(=O)_2(C_{1-3})$alkyl, carboxy, $(C_{1-4})$-alkoxycarbonyl, $(C_{1-4})$alkylcarbamoyl, $(C_{1-4})$alkylcarbonyloxy, $(C_{1-4})$alkylcarbonyl, hydroxyl-$(C_{1-4})$alkyl and optionally substituted amino.

Optional substituents on amino groups can be one or two groups independently selected from $(C_{1-4})$alkyl, $(C_{1-4})$alkoxy ($C_{1-4}$)alkyl, ($C_{1-4}$)alkoxycarbonyl, aryl($C_{1-4}$)alkoxycarbonyl and heteroaryl($C_{1-4}$)alkoxycarbonyl.

Optional substituents on carbamoyl can be one or two groups selected from ($C_{1-4}$)alkyl and ($C_{1-4}$)alkoxy($C_{1-4}$)alkyl.

Aryl is naphthyl or preferably phenyl. It can also be fused with a cycloalkyl or a heteroaromatic ring (e. g. to form a quinolyl or indolyl group).

Heteroaryl is an aromatic 5- or 6-membered ring, in which 1, 2 or 3 ring atoms are hetero atoms independently selected from O, N and S, such as thiazolyl, oxazolyl or preferably pyridyl. It can also be fused with a cycloalkyl or an aromatic or heteroaromatic ring (e. g. to form a quinolyl or indolyl group).

Any non-cyclic carbon containing group or moiety with more than 1 carbon atom is straight-chain or branched.

Unless defined otherwise, carbon containing groups, moieties or molecules contain 1 to 8, preferably 1 to 6, more preferably 1 to 4, most preferably 1 or 2, carbon atoms.

In preferred embodiments, the invention relates to a compound of the formula I, in free base form or in acid addition salt form, in which (1) $R_1$ is $(CH_2)_k N(R_a)R_b$ and $R_a$, $R_b$ and k have one of the meanings defined hereinbefore;

(2) $R_1$ is $(CH_2)_k N(R_a)R_b$, $R_a$ and $R_b$ have one of the meanings defined hereinbefore and k is 0;

(3) $R_1$ is $(CH_2)_k N(R_a)R_b$, k and $R_b$ have one of the meanings defined hereinbefore and $R_a$ is hydrogen;

(4) $R_1$ is $(CH_2)_k N(R_a)R_b$, k and $R_a$ have one of the meanings defined hereinbefore and $R_b$ is an optionally substituted ($C_{3-7}$)cycloalkyl, aryl($C_{1-4}$)alkyl, heteroaryl($C_{1-4}$)alkyl or chroman-4-yl group, preferably an optionally substituted ($C_{3-7}$)cycloalkyl, phenyl($C_{1-4}$)alkyl, pyridyl($C_{1-4}$)alkyl or chroman-4-yl group, more preferably an optionally substituted ($C_{3-6}$)cycloalkyl, phenyl($C_{1-2}$)alkyl, pyridyl($C_{1-2}$)alkyl or chroman-4-yl group, preferably a ($C_{3-6}$)cycloalkyl, phenyl($C_{1-2}$)alkyl, pyridyl($C_{1-2}$)alkyl or chroman-4-yl group optionally substituted by 1 to 4 substituents, independently selected from the group, consisting of ($C_{1-8}$)alkyl, ($C_{3-7}$)cycloalkyl, halogen and optionally substituted aryl, more preferably ($C_{3-6}$)cycloalkyl substituted by 1 or 2 substituents, independently selected from the group, consisting of optionally substituted aryl, preferably cyclopropyl substituted by 1 or 2 substituents, independently selected from the group, consisting of optionally substituted aryl, more preferably cyclopropyl substituted by 1 or 2 substituents, independently selected from the group, consisting of substituted phenyl, preferably cyclopropyl substituted by 1 or 2 substituents, independently selected from the group, consisting of phenyl substituted by 1 or 2 substituents, independently selected from the group, consisting of ($C_{1-8}$)alkyl and halogen, more preferably cyclopropyl substituted in 1-position by 3-($C_{1-8}$)alkylphenyl or 3-halogenphenyl, more preferably cyclopropyl substituted in 1-position by 3-tert-butylphenyl, more preferably cyclopropyl substituted in 1-position by 3-bromphenyl, more preferably phenyl($C_{1-2}$)alkyl optionally substituted by 1 or 2 substituents, independently selected from the group, consisting of ($C_{1-8}$)alkyl, preferably benzyl or 3-($C_{1-8}$)alkylbenzyl, more preferably benzyl, more preferably 3-isopropylbenzyl, more preferably 3-tert-butyl-benzyl, more preferably pyridyl($C_{1-2}$)alkyl optionally substituted by 1 or 2 substituents, independently selected from the group, consisting of ($C_{3-7}$)cycloalkyl, preferably pyridylmethyl substituted by 1 or 2 substituents, independently selected from the group, consisting of ($C_{3-7}$)cycloalkyl, more preferably 5-($C_{3-7}$)cycloalkylpyrid-3-ylmethyl, more preferably 5-cyclopropylpyrid-3-ylmethyl, more preferably chroman-4-yl optionally substituted by 1 to 4 substituents, independently selected from the group, consisting of ($C_{1-8}$)alkyl and halogen, preferably chroman-4-yl substituted by 1 to 3 substituents, independently selected from the group, consisting of ($C_{1-8}$)-alkyl and halogen, more preferably 2,2,6-tri($C_{1-4}$)alkylchroman-4-yl, 2,2-di($C_{1-4}$)alkyl-6-halogen-chroman-4-yl or 6-halogen-chroman-4-yl, more preferably 2,2-dimethyl-6-isopropyl-chroman-4-yl, more preferably 6-bromo-2,2-dimethyl-chroman-4-yl, more preferably 6-bromochroman-4-yl;

(5) $R_3$ has one of the meanings defined hereinbefore, preferably $R_3$ is hydrogen;

(6) $V_1$ and $V_2$ have one of the meanings defined hereinbefore, preferably $V_1$ is hydrogen and $V_2$ is hydroxy;

(7) $X_1$ has one of the meanings defined hereinbefore, preferably $X_1$ is $CH_2$;

(8) $X_2$ has one of the meanings defined hereinbefore, preferably $X_2$ is ($C_{1-8}$)alkylene, O or C(=O)N($R_2$)—($C_{1-8}$)alkylenoxy attached via its carbonyl function to Y and attached via the oxygen atom of its alkylenoxy moiety to Ar, in which $R_2$ is hydrogen or ($C_{1-4}$)alkyl, more preferably ($C_{1-4}$)alkylene, O or C(=O)N(H)—($C_{2-6}$)alkylenoxy attached via its carbonyl function to Y and attached via the oxygen atom of its alkylenoxy moiety to Ar, more preferably $CH_2$, more preferably O, more preferably C(=O)N(H)—$(CH_2)_4$O attached via its carbonyl function to Y and attached via the oxygen atom of its $(CH_2)_4$O moiety to Ar;

(9) Y has one of the meanings defined hereinbefore, preferably Y is ($C_{1-10}$)alkylene, more preferably ($C_{1-8}$)alkylene, more preferably $(CH_2)_3$, more preferably $(CH_2)_4$, more preferably $(CH_2)_5$, more preferably $(CH_2)_6$, more preferably $(CH_2)_7$, more preferably $CH_2C(H)CH_3$;

(10) Ar has one of the meanings defined hereinbefore, preferably Ar is unsubstituted phenylene, to which $X_1$ and $X_2$ are attached in meta or para position, preferably in meta position, to each other;

(11) Z, AA and n have one of the meanings defined hereinbefore, preferably either Z is C(=O), M is N[($C_{1-4}$)alkyl or ($C_{3-7}$)cycloalkyl]CH[($C_{1-4}$)alkyl]C(=O) and n is 0 or 1 or Z is S(=O)$_2$, AA is $CH_2$CH[($C_{1-4}$)alkyl]C(=O) and n is 1, more preferably Z is C(=O) and n is 0, more preferably Z is C(=O), AA is N($CH_3$)CH($CH_3$)C(=O) and n is 1, more preferably Z is C(=O), M is N(cyclopropyl)CH($CH_3$)C(=O) and n is 1, more preferably Z is S(=O)$_2$, M is $CH_2$CH($CH_3$)C(=O) and n is 1;

(12) the number of ring atoms included in the macrocyclic ring is 14;

(13) the number of ring atoms included in the macrocyclic ring is 15;

(14) the number of ring atoms included in the macrocyclic ring is 16;

(15) the number of ring atoms included in the macrocyclic ring is 17;

(16) the number of ring atoms included in the macrocyclic ring is 18.

The preferred embodiments (1) to (16) are preferred independently, collectively or in any combination or sub-combination.

In especially preferred embodiments, the invention relates to one or more than one of the compounds of the formula I mentioned in the Examples hereinafter, in free base form or in acid addition salt form.

In a further aspect, the invention relates to a process for the preparation of the compounds of the formula I and their salts, comprising the steps of
a) for the preparation of a compound of the formula I, in which Z is C(=O), cyclisation by amide formation of a compound of the formula

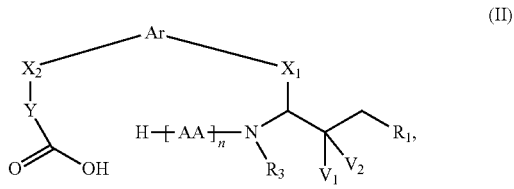
(II)

in which $R_1$, $R_3$, $V_1$, $V_2$, $X_1$, $X_2$, Y, Ar, AA and n are as defined for the formula I, or
b) for the preparation of a compound of the formula I, in which Z is $S(O=)_2$ and Y is $(C_{1-10})$alkenylene or $(C_{1-8})$alkenyloxy$(C_{1-6})$alkylene, cyclisation by metathesis of a compound of the formula

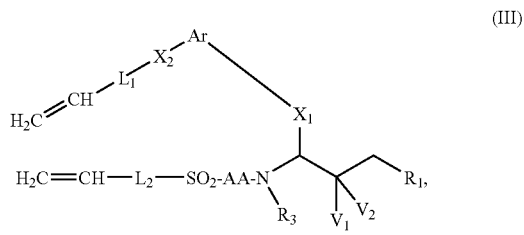
(III)

in which $R_1$, $R_3$, $V_1$, $V_2$, $X_1$, $X_2$, Ar and AA are as defined for the formula I and $L_1$ and $L_2$ are moieties selected in such a way, that the moiety $L_1CH=CHL_2$ corresponds to Y as defined for the formula I, or
c) for the preparation of a compound of the formula I, in which Z is $S(=O)_2$ and Y is $(C_{1-10})$-alkylene or $(C_{1-8})$alkyloxy$(C_{1-6})$alkylene, hydrogenation of a compound of the formula I, in which Z is $S(=O)_2$ and Y is $(C_{1-10})$alkenylene or $(C_{1-8})$alkenyloxy$(C_{1-6})$alkylene, or
d) for the preparation of a compound of the formula I, in which $R_1$ is $N(R_a)R_b$, $V_1$ is hydrogen and $V_2$ is hydroxy, reaction of a compound of the formula

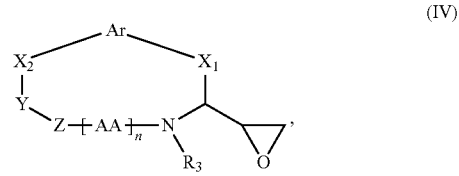
(IV)

in which $R_3$, $X_1$, $X_2$, Y, Z, Ar, AA and n are as defined for the formula I, with a compound of the formula $HN(R_a)R_b$ (V), in which $R_a$ and $R_b$ are as defined for the formula I,
in each case optionally followed by reduction, oxidation or functionalisation of the resulting compound and/or by cleavage of protecting groups optionally present, and of recovering the so obtainable compound of the formula I in free base form or in acid addition salt form.

The reactions can be effected according to conventional methods, for example as described in the Examples.

The working-up of the reaction mixtures and the purification of the compounds thus obtainable may be carried out in accordance with known procedures.

Acid addition salts may be produced from the free bases in known manner, and vice-versa.

Compounds of the formula I can also be prepared by further conventional processes, which processes are further aspects of the invention, e. g. as described in the Examples.

The starting materials of the formulae II, III, IV and V are known or may be prepared according to conventional procedures starting from known compounds, for example as described in the Examples.

Compounds of the formula I and their pharmaceutically acceptable acid addition salts, hereinafter referred to as "agents of the invention", exhibit valuable pharmacological properties when tested in vitro and in animals, and are therefore useful as medicaments.

The agents of the invention are inhibitors of aspartic proteases and can be used for the treatment of disorders involving processing by such enzymes. Particularly they inhibit beta-secretase and as such inhibit the generation of beta-amyloid and the subsequent aggregation into oligomers and fibrils.

Test 1: Inhibition of Human BACE

Recombinant BACE (extracellular domain, expressed in baculovirus and purified using standard methods) at 6 nM concentration is incubated with the test compound at various concentrations for 1 hour at room temperature in 100 mM acetate buffer, pH 4.5, containing 0.1% CHAPS. Synthetic peptide substrate Mca-Ser-Glu-Val-Asn-Leu-Asp-Ala-Glu-Phe-Lys(DNP) (SEQ ID NO: 1) is added to a final concentration of 3 µM and the increase in fluorescence is recorded at excitation of 325 nm and emission at 400 nm in a microplate spectro-fluorimeter for 20 minutes in 1-minute intervals. $IC_{50}$ values are calculated from percentage of inhibition of BACE-activity as a function of the test compound concentration.

Test 2: Inhibition of Human BACE-2

Recombinant BACE-2 (extracellular domain, expressed in baculovirus and purified using standard methods) at 2.5 nM concentrations is incubated with the test compound at various concentrations for 1 hour at room temperature in 100 mM acetate buffer, pH 4.5, containing 0.1% CHAPS. Synthetic peptide substrate Mca-Ser-Glu-Val-Asn-Leu-Asp-Ala-Glu-Phe-Lys(DNP) (SEQ ID NO: 1) is added to a final concentration of 3 µM and the increase in fluorescence is recorded at excitation of 325 nm and emission at 400 nm in a microplate spectro-fluorimeter for 20 minutes in 1-minute intervals. $IC_{50}$ values are calculated from percentage of inhibition of BACE-2-activity as a function of the test compound concentration.

Test 3: Inhibition of Human Cathepsin D

Recombinant cathepsin D (expressed as procathepsin D in baculovirus, purified using standard methods and activated by incubation in sodium formate buffer pH 3.7) is incubated with the test compound at various concentrations for 1 hour at room temperature in 100 mM sodium formate buffer, pH 3.1. Synthetic peptide substrate Mca-Gly-Lys-Pro-Ile-Leu-Phe-Phe-Arg-Leu-Lys(DNP)-D-Arg-$NH_2$ is added to a final concentration of 2 µM and the increase in fluorescence is recorded at excitation of 325 nm and emission at 400 nm in a microplate spectro-fluorimeter for 20 minutes in 1-minute intervals. $IC_{50}$ values are calculated from percentage of inhibition of cathepsin D-activity as a function of the test compound concentration.

Test 4: Inhibition of Cellular Release of Amyloid Peptide 1-40

Chinese hamster ovary cells are transfected with the gene for amyloid precursor protein. Cells are plated at a density of 8000 cells/well in a 96-well microtiter plate and cultivated for 24 hours in DMEM cell culture medium containing 10% FCS. The test compound is added to the cells at various concentrations, and cells are cultivated for 24 hours in the presence of the test compound. The supernatants are collected, and the concentration of amyloid peptide 1-40 is determined using sandwich ELISA. The potency of the compound is calculated from the percentage of inhibition of amyloid peptide release as a function of the test compound concentration.

In at least one of the above-indicated tests, the agents of the invention show activity at concentrations below 20 µM.

Specifically, the compound I described in Example 4 shows an $IC_{50}$ value of 0.25 µM.

The agents of the invention are therefore useful e. g. for the treatment and/or prevention of neurological and vascular disorders related to beta-amyloid generation and/or aggregation, such as neurodegenerative diseases like Alzheimer's disease, Down's Syndrome, memory and cognitive impairment, dementia, amyloid neuropathies, brain inflammation, nerve and brain trauma, vascular amyloidosis, or cerebral haemorrhage with amyloidosis.

Some of the agents of the invention also inhibit BACE2 (beta-site APP-cleaving enzyme 2) or Cathepsin D, close homologues of the pepsin-type aspartyl proteases and of beta-secretase. Due to the correlation of BACE2 and CathD expression with a more tumorigenic and metastatic potential of tumor cells, such inhibitors are useful for the suppression of the metastasis process associated with tumor cells.

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100, preferably from about 1 to about 50, mg/kg of animal body weight. In larger mammals, for example humans, an indicated daily dosage is in the range from about 10 to about 2000, preferably from about 10 to about 200, mg of an agent of the invention conveniently administered, for example, in divided doses up to four times a day or in sustained release form.

The agent of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a medicament, e. g. for the treatment of neurological or vascular disorders related to beta-amyloid generation and/or aggregation.

The present invention furthermore provides a pharmaceutical composition comprising an agent of the invention in association with at least one pharmaceutical carrier or diluent. Such compositions may be manufactured in conventional manner. Unit dosage forms contain, for example, from about 1 to about 1000, preferably from about 1 to about 500, mg of an agent of the invention.

The agents of the invention can be administered alone or in combination with other pharmaceutical agents effective in the treatment of conditions mentioned above.

The pharmaceutical combination may be in the form of a unit dosage form, whereby each unit dosage will comprise a predetermined amount of the two components, in admixture with suitable pharmaceutical carriers or diluents. Alternatively, the combination may be in form of a package containing the two components separately, e. g. a pack or dispenser-device adapted for the concomitant or separate administration of the two active agents, wherein these agents are separately arranged.

Moreover the present invention provides the use of an agent of the invention, for the manufacture of a medicament for the treatment of any neurological or vascular disorders related to beta-amyloid generation and/or aggregation.

In still a further aspect, the present invention provides a method for the treatment of any neurological or vascular disorders related to beta-amyloid generation and/or aggregation, in a subject in need of such treatment, which comprises administering to such subject a therapeutically effective amount of an agent of the invention.

The following Examples illustrate the invention, but do not limit it.

EXAMPLES

| Abbreviations | |
|---|---|
| abs. | absolute |
| AcCN | acetonitrile |
| aq. | aqueous |
| $BH_3$-$SMe_2$ | borane-dimethyl sulfide complex |
| BOC | tert-butoxycarbonyl |
| conc. | concentrated |
| DBU | diazabicycloundecene |
| DCM | dichloromethane |
| DIPEA | diisopropylethylamine |
| DMF | dimethylformamide |
| DMPU | N,N'-dimethylpropylene urea |
| DMSO | dimethylsulfoxide |
| DPPA | diphenylphosphoryl azide |
| EDC.HCl | 1-ethyl-3-[3-(dimethylamino)propyl]-carbodiimide hydrochloride |
| eq | equivalent(s) |
| ES | electron spray |
| $Et_3N$ | triethylamine |
| $Et_2O$ | diethyl ether |
| EtOAc | ethyl acetate |
| EtOH | ethanol |
| Grubbs II catalyst | [1, 3-bis(2,4,6-trimethylphenyl)-2-imidazolidinylidene]dichloro(phenylmethylene)(triphenylphosphine)-ruthenium (CAS 331282-59-8) |
| h | hour(s) |
| HMDS | 1,1,1,3,3,3-hexamethyl-disilazane |
| $^1$H-NMR | proton nuclear magnetic resonance spectrometry |
| HOBt | hydroxybenzotriazole |
| HPLC | high pressure liquid chromatography |
| LC | liquid chromatography |
| LHMDS | lithium hexamethyldisilazide |
| MeOH | methanol |
| min | minute(s) |
| m. p. | melting point |
| MS | mass spectrometry |
| $NH_3$ | 14 N aqueous ammonia |
| Pd/C | palladium on charcoal |
| PE 40-60 | petrolether |
| PPTS | pyridinium-para-toluenesulfonate |
| Rf | retention factor (thin layer chromatography) |
| rt | room temperature |
| SK-CC02-A | 2-(dimethylamino)ferrocen-1-yl-palladium(II)chloride dinorbornylphosphine complex (CAS 614753-51-4) |
| TBME | tert-butyl methyl ether |
| tBuOH | tert-butanol |
| TFA | trifluoroacetic acid |
| $Tf_2O$ | trifluoromethanesulfonic acid anhydride |
| THF | tetrahydrofuran |

Example 1

(10S,13S)-13-[(R)-1-Hydroxy-2-(3-isopropyl-benzylamino)-ethyl]-9,10-dimethyl-2-oxa-9,12-diaza-bicyclo[13.3.1]nonadeca-1(19),15,17-triene-8,11-dione a) (2S,3S)-4-(3-Allyloxy-phenyl)-3-amino-1-chloro-butan-2-ol hydrochloride

A solution of 2.23 g (6.26 mmol) of [(1S,2S)-1-(3-allyloxy-benzyl)-3-chloro-2-hydroxy-propyl]-carbamic acid tert-butyl ester (building block B1) in 63 ml of DCM is cooled to 0° C. 12.6 ml of 5 M HCl in Et$_2$O (63 mmol) are added, and the mixture is stirred at rt for 1.5 h. The solvent is evaporated, and the residue is crystallized from Et$_2$O to give the product in the form of pale brownish crystals.

m. p.: 132-135° C.
Rf (DCM/MeOH/NH$_3$=90/9/1): 0.39.
MS (ES+): 256.1=[M+H]$^+$.
$^1$H-NMR (400 MHz, DMSO-d$_6$): 7.79 (br s, 3H), 7.24 (t, 1H), 6.90-6.71 (m, 3H), 6.09-5.98 (m, 2H), 5.39 (dd, 1H), 5.25 (dd, 1H), 4.56 (d, 2H), 3.95-3.89 (m, 1H), 3.71 (dd, 1H), 3.56-3.47 (m, 2H), 2.93 (dd, 1H), 2.72 (dd, 1H).

b) {(S)-1-[(1S,2S)-1-(3-Allyloxy-benzyl)-3-chloro-2-hydroxy-propylcarbamoyl]-ethyl}-methyl-carbamic acid tert-butyl ester To a stirred solution of 407 mg (2 mmol) of BOC-N-methyl-(L)-alanine, 443 mg (2.8 mmol) of HOBt, 584 mg (2 mmol) of (2S,3S)-4-(3-allyloxy-phenyl)-3-amino-1-chloro-butan-2-ol hydrochloride and 0.379 ml (2.2 mmol) of DIPEA in 15 ml of DCM/THF (2/1) at 0° C. are added 422 mg (2.2 mmol) of EDC.HCl. The mixture is allowed to warm to rt and then stirred for 16 h. 20 ml of DCM and 10 ml of 0.5 M HCl are added, and the layers are separated. The aq. phase is extracted with 10 ml of DCM/EtOH (80/20), and the combined organic layers are washed with 1 M potassium bicarbonate and water, dried over sodium sulfate and evaporated to give the product in the form of a brownish oil.

Rf (DCM/MeOH/NH$_3$=95/4.5/0.5): 0.55.

c) (S)—N-[(1S,2S)-1-(3-Allyloxy-benzyl)-3-chloro-2-hydroxy-propyl]-2-methylamino-propionamide hydrochloride A solution of 890 mg (2 mmol) of {(S)-1-[(1S,2S)-1-(3-allyloxy-benzyl)-3-chloro-2-hydroxy-propylcarbamoyl]-ethyl}-methyl-carbamic acid tert-butyl ester in 10 ml of DCM is cooled to 0° C., and 4.8 ml of 5 M HCl in Et$_2$O (24 mmol) are added. The mixture is stirred at rt for 2 h. The solvent is evaporated, and the residue is crystallized from CH$_2$Cl$_2$ to give the product in the form of pale brownish crystals.

m. p.: 173-176° C.
Rf (DCM/MeOH/NH$_3$=90/9/1): 0.42.
MS (ES+): 341.2=[M+H]$^+$.
$^1$H-NMR (400 MHz, DMSO-d$_6$): 8.65 (br s, 2H), 8.47 (d, 1H), 7.14 (t, 1H), 6.83-6.71 (m, 3H), 6.08-5.97 (m, 1H), 5.65 (d, 1H), 5.37 (dd, 1H), 5.24 (dd, 1H), 4.51 (d, 2H), 4.13-4.04 (m, 1H), 3.72-3.63 (m, 2H), 3.61-3.48 (m, 2H), 2.99 (dd, 1H), 2.62-2.53 (m, 1H), 2.09 (s, 3H), 1.30 (d, 3H).

d) Pent-4-enoic acid {(S)-1-[(1S,2S)-1-(3-allyloxy-benzyl)-3-chloro-2-hydroxy-propylcarbamoyl]-ethyl}-methyl-amide To a stirred solution of 118 mg (1.18 mmol) of pent-4-enoic acid, 237 mg (1.5 mmol) of HOBt, 404 mg (1.07 mmol) of (S)—N-[(1S,2S)-1-(3-allyloxy-benzyl)-3-chloro-2-hydroxy-propyl]-2-methylamino-propionamide hydrochloride and 0.2 ml (1.18 mmol) of DIPEA in 5 ml of DCM at 0° C. are added 226 mg (1.18 mmol) of EDC.HCl. The mixture is allowed to warm to rt and then stirred for 64 h. 22 ml of DCM/EtOH (90/10) are added, and the mixture is washed with 11 ml of 0.5 M HCl. The HCl phase is extracted with 11 ml of DCM/EtOH (90/10), and the combined organic layers are washed with 11 ml of 1 M potassium bicarbonate, dried over sodium sulfate and evaporated. The residue is purified by chromatography on silica gel (cyclohexane/EtOAc 90/10 to 80/20) to give the product in the form of a colorless sticky solid.

Rf (cyclohexane/EtOAc=50/50): 0.18.
MS (ES+): 423.3=[M+H]$^+$.
$^1$H-NMR (400 MHz, DMSO-d$_6$, major rotamer): 7.43 (d, 1H), 7.15-7.06 (m, 1H), 6.78-6.68 (m, 3H), 6.07-5.96 (m, 1H), 5.89-5.73 (m, 1H), 5.48 (d, 1H), 5.37 (dd, 1H), 5.07-4.85 (m, 3H), 4.51 (d, 2H), 4.07-3.93 (m, 1H), 3.70-3.57 (m, 2H), 3.48-3.40 (m, 1H), 2.96 (dd, 1H), 2.62 (dd, 1H), 2.40 (s, 3H), 2.35-2.12 (m, 4H), 1.03 (d, 3H).

e) (E/Z)-(10S,13S)-13-((S)-2-Chloro-1-hydroxy-ethyl)-9,10-dimethyl-2-oxa-9,12-diaza-bicyclo[13.3.1]nonadeca-1(19)4,15,17-tetraene-8,11-dione A solution of 285 mg (0.67 mmol) of pent-4-enoic acid {(S)-1-[(1S,2S)-1-(3-allyloxy-benzyl)-3-chloro-2-hydroxy-propylcarbamoyl]-ethyl}-methyl-amide in 4 ml of DCM is added dropwise within 1 h to a refluxing solution of 29 mg of Grubbs II catalyst in 67 ml of DCM. The mixture is then refluxed for 5 h and evaporated. The residue is purified by chromatography on silica gel (DCM/MeOH 99/1 to 98/2) to give the product in the form of a grayish foam.

Rf (DCM/MeOH=95/5): 0.33.

f) (10S,13S)-3-((S)-2-Chloro-1-hydroxy-ethyl)-9,10-dimethyl-2-oxa-9,12-diaza-bicyclo[13.3.1]nonadeca-1(19),15,17-triene-8,11-dione A solution of 226 mg (0.57 mmol) of (E/Z)-(10S,13S)-13-((S)-2-chloro-1-hydroxy-ethyl)-9,10-dimethyl-2-oxa-9,12-diaza-bicyclo[13.3.1]nonadeca-1(19),4,15,17-tetraene-8,11-dione in 12 ml of EtOH is stirred at rt for 2 h under a hydrogen atmosphere in the presence of 115 mg of 10% Pd/C. The catalyst is filtered off, and the filtrate is evaporated to give the product in the form of a colorless foam.

Rf (DCM/MeOH/NH$_3$=90/9/1): 0.59.
MS (LC/MS): 395.1=[M−H]$^−$.

g) (10S,13S)-9,10-Dimethyl-13-(S)-oxiranyl-2-oxa-9,12-diaza-bicyclo[13.3.1]nonadeca-1(19),15,17-triene-8,11-dione To a solution of 110 mg (0.28 mmol) of (10S,13S)-13-((S)-2-chloro-1-hydroxy-ethyl)-9,10-dimethyl-2-oxa-9,12-diaza-bicyclo[13.3.1]nonadeca-1(19),15,17-triene-8,11-dione in 2.8 ml of THF are added 0.6 ml of 1 M NaOH dropwise at 0° C. The mixture is stirred for 4 h at 0° C. 2.8 ml of saturated ammonium chloride solution are added, the mixture is extracted with DCM, and the combined organic layers are washed with 2.8 ml of water, dried over sodium sulfate and evaporated to give the product in the form of a colorless foam.

Rf (DCM/MeOH/NH$_3$=90/9/1): 0.68.
MS (ES+): 361=[M+H]$^+$.
$^1$H-NMR (400 MHz, DMSO-d$_6$, major conformer): 7.77 (d, 1H), 7.16-7.10 (m, 1H), 6.81-6.69 (m, 3H), 4.97-4.90 (m, 1H), 4.07-4.00 (m, 2H), 3.81-3.72 (m, 1H), 3.62-3.56 (m, 1H), 2.92-2.87 (m, 2H), 2.74-2.56 (m, 5H), 2.05-1.95 (m, 2H), 1.81-1.68 (m, 4H), 1.59-1.46 (m, 2H), 0.98 (d, 3H).

h) (10S,13S)-13-[(R)-1-Hydroxy-2-(3-isopropyl-benzylamino)-ethyl]-9,10-dimethyl-2-oxa-9,12-diaza-bicyclo[13.3.1]nonadeca-1(19),15,17-triene-8,11-dione A solution of 40 mg (0.11 mmol) of (10S,13S)-9,10-dimethyl-13-(S)-oxiranyl-2-oxa-9,12-diaza-bicyclo[13.3.1]nonadeca-1(19),15,17-triene-8,11-dione in 66 mg (0.44 mmol) of 3-isopropyl-benzylamine is heated to 80° C. for 20 h. Excess amine is removed by addition of toluene and evaporation of the solvent. The residue is purified by chromatography on silica gel (DCM/methanol/$NH_3$ 99/0.9/0.1 to 95/4.5/0.5) to give the product.

Rf (DCM/MeOH/$NH_3$=95/4.5/0.5): 0.28.
MS (ES+): 510.0=[M+H]$^+$.
$^1$H-NMR (400 MHz, DMSO-$d_6$, major conformer): 7.79 (d, 1H), 7.40-7.24 (m, 5H), 7.14 (t, 1H), 6.77-6.68 (m, 3H), 5.72 (br, 1H), 4.94-4.87 (m, 1H), 4.15-3.98 (m, 4H), 3.90-3.80 (m, 1H), 3.72-3.64 (m, 1H), 3.09-3.01 (m, 1H), 2.96-2.84 (m, 2H), 2.83-2.73 (m, 1H), 2.25 (s, 3H), 2.23-2.12 (m, 1H), 2.05-1.96 (m, 1H), 1.82-1.65 (m, 2H), 1.62-1.32 (m, 5H), 1.21 (d, 6H), 0.92 (d, 3H).

The following compounds 1a to 1e can be prepared by an analogous reaction sequence as described for example 1, using in step h) instead of 3-isopropyl-benzylamine either benzylamine, 1-(3-bromo-phenyl)-cyclopropylamine (building block C3), (R/S)-6-isopropyl-2,2-dimethyl-chroman-4-ylamine (building block C5), (R/S)-6-bromo-2,2-dimethyl-chroman-4-ylamine (building block C8) or (S)-6-isopropyl-2,2-dimethyl-chroman-4-ylamine (building block C7).

Example 1a (10S,13S)-13-((R)-2-Benzylamino-1-hydroxy-2-ethyl]-9,10-dimethyl-2-oxa-9,12-diaza-bicyclo[13.3.1]nonadeca-1(19),15,17-triene-8,11-dione Rf (DCM/MeOH/$NH_3$=90/9/1): 0.34.
MS (ES+): 468.0=[M+H]$^+$.
$^1$H-NMR (400 MHz, DMSO-$d_6$, major conformer): 7.59 (d, 1H), 7.33-7.24 (m, 4H), 7.22-7.16 (m, 1H), 7.11 (t, 1H), 6.77-6.65 (m, 3H), 4.95-4.87 (m, 1H), 4.79 (br, 1H), 4.05-3.97 (m, 2H), 3.92-3.79 (m, 1H), 3.69 (s, 2H), 3.49-3.40 (m, 1H), 3.00-2.93 (m, 1H), 2.54-2.39 (m, 2H), 2.34 (s, 3H), 2.29-1.92 (m, 3H), 1.81-1.64 (m, 2H), 1.61-1.22 (m, 5H), 0.91 (d, 3H).

Example 1b (10S,13S)-13-{(R)-2-[1-(3-Bromo-phenyl)-cyclopropylamino]-1-hydroxy-ethyl}-9,10-dimethyl-2-oxa-9,12-diaza-bicyclo[13.3.1]nonadeca-1(19),15,17-triene-8,11-dione Rf (DCM/MeOH/$NH_3$=90/9/1): 0.59.
MS (ES+): 574.0=[M+H]$^+$.
$^1$H-NMR (400 MHz, DMSO-$d_6$, major conformer): 7.96 (d, 1H), 7.79 (1H), 7.63-7.53 (m, 2H), 7.38 (t, 1H), 7.12 (t, 1H), 6.78-6.66 (m, 3H), 5.76 (br, 1H), 4.89-4.82 (m, 1H), 4.09-3.96 (m, 2H), 3.82-3.71 (m, 1H), 3.68-3.59 (m, 1H), 3.06-3.00 (m, 1H), 2.86-2.61 (m, 2H), 2.54-2.42 (m, 1H), 2.23 (s, 3H), 2.21-2.12 (m, 1H), 2.03-1.94 (m, 1H), 1.83-1.62 (m, 4H), 1.60-1.15 (m, 6H), 0.85 (d, 3H).

Example 1c (10S,13S)-13-[(R)-1-Hydroxy-2-((R/S)-6-isopropyl-2,2-dimethyl-chroman-4-ylamino)-ethyl]-9,10-dimethyl-2-oxa-9,12-diaza-bicyclo[13.3.1]nonadeca-1(19),15,17-triene-8,11-dione Rf (DCM/MeOH/$NH_3$=9514.5/0.5): 0.17.
MS (ES+): 580.0=[M+H]$^+$.
$^1$H-NMR (400 MHz, DMSO-$d_6$, 2 diasteromers): 7.93 (d, 1H), 7.40-7.36 (m, 1H), 7.14 (t, 1H), 6.95-6.90 (m, 1H), 6.83-6.72 (m, 2H), 6.59-6.55 (m, 1H), 4.9 (br, 1H), 4.17-4.10 (m, 2H), 4.03-3.92 (m, 1H), 3.84-3.75 (m, 1H), 3.50-3.35 (m, 3H), 3.09-3.02 (m, 1H), 2.96-2.73 (m, 4H), 2.70-2.55 (m, 3H), 2.12-2.05 (m, 0.5H), 2.02-1.96 (m, 0.5H), 1.90 (s, 2H), 1.83-1.67 (m, 5H), 1.65-1.57 (m, 0.5H), 1.54-1.46 (m, 0.5H), 1.36 (s, 3H), 1.28 (s, 3H), 1.13 (d, 1.5H), 1.07 (d, 1.5H).

Example 1d (10S,13S)-13-[(R)-2-((R/S)-6-bromo-2,2-dimethyl-chroman-4-ylamino)-1-hydroxy-ethyl]-9,10-dimethyl-2-oxa-9,12-diaza-bicyclo[13.3.1]nonadeca-1(19),15,17-triene-8,11-dione Rf (DCM/MeOH/$NH_3$=95/4.5/0.5): 0.39.
MS (ES+): 618.0=[M+H]$^+$.

Example 1e (10S,13S)-13-[(R)-1-Hydroxy-2-((S)-6-isopropyl-2,2-dimethyl-chroman-4-ylamino)-ethyl]-9,10-dimethyl-2-oxa-9,12-diaza-bicyclo[13.3.1]nonadeca-1(19),15,17-triene-8,11-dione Rf (DCM/MeOH=90/10): 0.56.
MS (ES+): 580.0=[M+H]$^+$.
$^1$H-NMR (400 MHz, DMSO-$d_6$, major conformer): 7.88 (d, 1H), 7.66 (s, 1H), 7.37 (t, 1H), 7.21-7.16 (m, 1H), 7.06-6.92 (m, 3H), 6.86-6.81 (m, 1H), 5.24-5.13 (m, 1H), 5.07-4.99 (m, 1H), 4.39-4.13 (m, 3H), 4.08-3.99 (m, 1H), 3.79-3.68 (m, 1H), 3.30-3.20 (m, 1H), 3.09-3.01 (m, 1H), 2.96-2.78 (m, 3H), 2.59 (s, 3H), 2.52-2.43 (m, 1H), 2.36 (dd, 1H), 2.30-2.20 (m, 2H), 2.06-1.92 (m, 2H), 1.87-1.55 (m, 10H), 1.46-1.39 (m, 12H).

The following compounds 2a to 2d can be prepared by an analogous reaction sequence as described for example 1, starting from [(1S,2S)-1-(3-allyloxy-benzyl)-3-chloro-2-hydroxy-propyl]-carbamic acid tert-butyl ester (building block B1), using in step d) instead of pent-4-enoic acid either hept-6-enoic acid, hex-5-enoic acid, but-3-enoic acid or acrylic acid.

Example 2a (12S,15S)-15-[(R)-1-Hydroxy-2-(3-isopropyl-benzylamino)-ethyl]-11,12-dimethyl-2-oxa-11,14-diaza-bicyclo[15.3.1]henicosa-1(21),17,19-triene-10,13-dione MS (ES+): 538=[M+H]$^+$.
1H-NMR (400 MHz, CDCl$_3$): 7.27-7.10 (m, 5H), 6.82 (d, 1H), 6.70-6.60 (m, 2H), 6.02 (d, 1H), 5.14 (ddd, 1H), 4.28-4.18 (m, 1H), 4.05-3.95 (m, 2H), 3.80 (d, 2H), 3.62 (s, 3H), 3.62-3.40 (m, 4H), 3.22 (dd, 1H), 2.95 (m, 1H), 2.72 (m, 2H), 2.53 (dd, 1H), 2.20-1.50 (m, 9H), 1.35-1.08 (m, 9H).

Example 2b (11S,14S)-14-[(R)-1-Hydroxy-2-(3-isopropyl-benzylamino)-ethyl]-10,11-dimethyl-2-oxa-10,13-diazabicyclo[14.3.1]icosa-1(20),16,18-triene-9,12-dione MS (ES+): 524=[M+H]$^+$.
1H-NMR (400 MHz, CDCl$_3$): 7.27-7.10 (m, 5H), 6.83 (d, 1H), 6.75 (dd, 1H), 6.58 (s, 1H), 5.95 (d, 1H), 5.13 (ddd, 1H), 4.30-4.18 (m, 1H), 4.18-4.05 (m, 1H), 4.05-3.98 (m, 1H), 3.80 (d, 2H), 3.62 (s, 3H), 3.62-3.54 (m, 2H), 3.50-3.40 (m, 2H), 3.09 (dd, 1H), 2.95 (m, 1H), 2.71 (m, 2H), 2.15-2.05 (m, 1H), 2.05-1.90 (m, 1H), 1.90-1.60 (m, 3H), 1.60-1.40 (m, 3H), 1.35-1.08 (m, 9H).

Example 2c (9S,12S)-12-[(R)-1-Hydroxy-2-(3-isopropyl-benzylamino)-ethyl]-8,9-dimethyl-2-oxa-8,11-diaza-bicyclo[12.3.1]octadeca-1(18),14,16-triene-7,10-dione HPLC [(Nucleosil C-18HD, 4×70 mm, 3 μm, 1 ml/min, 20-100% AcCN (6 min)] retention time: 3.76 min.
MS (ES+): 496=[M+H]$^+$.

Example 2d (8S,11S)-11-[(R)-1-Hydroxy-2-(3-isopropyl-benzylamino)-ethyl]-7,8-dimethyl-2-oxa-7,10-diaza-bicyclo[11.3.1]heptadeca-1(17),13,15-triene-6,9-dione HPLC [(Nucleosil C-18HD, 4×70 mm, 3 μm, 1 ml/min, 20-100% AcCN (6 min)] retention time: 3.82 min.
MS (ES+): 482=[M+H]$^+$.

Example 3

(10S,13S)-9-Cyclopropyl-13-[(R)-1-hydroxy-2-(3-isopropyl-benzylamino)-ethyl]-10-methyl-2-oxa-9,12-diaza-bicyclo[13.3.1]nonadeca-1(19),15,17-triene-8,11-dione The title compound can be prepared by an analogous reaction sequence as described for example 1, starting from [(1S,2S)-1-(3-allyloxy-benzyl)-3-chloro-2-hydroxy-propyl]-carbamic acid tert-butyl ester (building block B1) and using (S)-2-(tert-butoxycarbonyl-cyclopropyl-amino)-propionic acid (building block A3) in step b) instead of BOC-N-methyl-(L)-alanine. LC/MS [(Nucleosil C-18HD, 4×70 mm, 3 μm, 1 ml/min, 20-100% AcCN (6 min)] retention time: 4.56 min.
MS (ES+): 536=[M+H]$^+$.

Example 4

(3S,6S)-3-[(R)-1-Hydroxy-2-(3-isopropyl-benzylamino)-ethyl]-6,7-dimethyl-4,7-diaza-bicyclo[13.3.1]nonadeca-1(18),15(19),16-triene-5,8-dione The title compound can be prepared by an analogous reaction sequence as described for example 1, starting from [(1S,2S)-1-(3-allyl-benzyl)-3-chloro-2-hydroxy-propyl]-carbamic acid tert-butyl ester (building block B2) instead of [(1S,2S)-1-(3-allyloxy-benzyl)-3-chloro-2-hydroxy-propyl]-carbamic acid tert-butyl ester (building block B1) and using hex-5-enoic acid in step d) instead of pent-4-enoic acid.
Rf (DCM/MeOH/NH$_3$=95/4.5/0.5): 0.18.
MS (ES+): 508.6=[M+H]$^+$.

Example 4a (3S,6S)-3-{(R)-2-[(5-Cyclopropyl-pyridine-3-ylmethyl)-amino]-1-hydroxy-ethyl}-6,7-dimethyl-4,7-diaza-bicyclo[13.3.1]nonadeca-1(18),15(19),16-triene-5,8-dione The title compound can be prepared by an analogous reaction sequence as described for example 4, using C-(5-cyclopropyl-pyridin-3-yl)-methylamine (building block C2) in the last step instead of 3-isopropyl-benzylamine.
Rf (DCM/MeOH/NH$_3$=90/9/1): 0.38.
MS (ES+): 529.0=[M+Na]$^+$.
$^1$H-NMR (400 MHz, DMSO-d$_6$, major conformer): 7.31 (d, 1H), 5.85-5.69 (m, 2H), 5.33-5.25 (m, 1H), 5.03-4.86 (m, 5H), 3.89-3.74 (m, 1H), 3.62-3.45 (m, 2H), 3.43-3.32 (m, 1H), 2.82 (s, 3H), 2.34-2.16 (m, 2H), 2.07-1.95 (m, 4H), 1.55-1.20 (m, 13H), 1.17 (d, 3H), 0.90-0.74 (m, 3H).

Example 5

(3S,6S)-3-[(R)-1-Hydroxy-2-(3-isopropyl-benzylamino)-ethyl]-6,7-dimethyl-4,7-diaza-bicyclo[12.3.1]octadeca-1(17),14(18),15-triene-5,8-dione The title compound can be prepared by an analogous reaction sequence as described for example 1, starting from [(1S,2S)-1-(3-allyl-benzyl)-3-chloro-2-hydroxy-propyl]-carbamic acid tert-butyl ester (building block B2) instead of [(1S,2S)-1-(3-allyloxy-benzyl)-3-chloro-2-hydroxy-propyl]-carbamic acid tert-butyl ester (building block B1).
Rf (DCM/MeOH=90/10): 0.38.
MS (ES+): 494.0=[M+H]$^+$.
$^1$H-NMR (400 MHz, DMSO-d$_6$, major conformer): 7.60 (d, 1H), 7.23-7.17 (m, 2H), 7.15-7.05 (m, 3H), 6.99-6.88 (m, 3H), 4.97-4.89 (m, 1H), 4.87 (br, 1H), 3.99-3.88 (m, 1H), 3.74-3.63 (m, 2H), 3.53-3.45 (m, 1H), 3.09-2.97 (m, 1H), 2.90-2.81 (m, 1H), 2.60-2.32 (m, 4H), 2.46 (s, 3H), 2.00-1.74 (m, 4H), 1.67-1.51 (m, 3H), 1.49-1.32 (m, 3H), 1.20 (d, 6H), 0.95 (d, 3H).

Example 6

(9S,12S)-12-[(R)-1-Hydroxy-2-(3-isopropyl-benzylamino)-ethyl]-9-methyl-7,7-dioxo-2-oxa-7lambda*6*-thia-11-aza-bicyclo[12.3.1]octadeca-1(18),14,16-trien-10-one The title compound can be prepared by an analogous reaction sequence as described for example 1, starting from [(1S,2S)-1-(3-allyloxy-benzyl)-3-chloro-2-hydroxy-propyl]-carbamic acid tert-butyl ester (building block B1) and using (S)-2-methyl-3-(prop-2-en-1-ylsulfonyl)-propionic acid (building block A4) in step b) instead of BOC-N-methyl-(L)-alanine, followed by ring-closing metathesis and subsequent reaction steps.
m. p.: 148-150° C.
Rf (DCM/MeOH=90/10): 0.19.
MS (ES+): 517=[M+H]$^+$.
$^1$H-NMR (400 MHz, DMSO-d$_6$): 7.88 (d, 1H), 7.22-7.04 (m, 5H), 6.79 (s, 1H), 6.77-6.71 (m, 2H), 4.91 (br, 1H), 4.18-4.08 (m, 2H), 3.93-3.82 (m, 1H), 3.72-3.62 (m, 2H), 3.47-3.38 (m, 1H), 3.30-3.19 (m, 1H), 3.05-2.99 (m, 1H), 2.97-2.80 (m, 3H), 2.78-2.69 (m, 1H), 2.67-2.42 (m, 4H), 1.83-1.67 (m, 4H), 1.20 (d, 6H), 1.03 (d, 3H).

The following compounds 6a to 6c can be prepared by an analogous reaction sequence as described for example 6, starting from [(1S,2S)-1-(3-allyloxy-benzyl)-3-chloro-2-hydroxy-propyl]-carbamic acid tert-butyl ester (building block B1) and using in the final step instead of 3-isopropyl-benzylamine either 1-(3-bromo-phenyl)-cyclopropylamine (building block C3), (R/S)-6-isopropyl-2,2-dimethyl-chroman-4-ylamine (building block C5) or (R/S)-6-bromo-chroman-4-ylamine (building block C6).

Example 6a (9S,12S)-12-{(R)-2-[1-(3-Bromo-phenyl)-cyclopropylamino]-1-hydroxy-ethyl}-9-methyl-7,7-dioxo-2-oxa-7lambda*6*-thia-1-aza-bicyclo[12.3.1]octadeca-1(18),14,16-trien-10-one Rf (DCM/MeOH=95/5): 0.22.
MS (ES+): 579/581=[M+H]$^+$.
$^1$H-NMR (400 MHz, DMSO-d$_6$): 8.06 (d, 1H), 7.78 (s, 1H), 7.60 (d, 1H), 7.53 (d, 1H), 7.38 (t, 1H), 7.16 (t, 1H), 6.79-6.70 (m, 3H), 5.80 (d, 1H), 4.18-4.08 (m, 2H), 3.83-3.73 (m, 1H), 3.64-3.55 (m, 1H), 3.18-3.03 (m, 3H), 2.96-2.77 (m, 3H), 2.74-2.61 (m, 3H), 2.54-2.37 (m, 1H), 1.83-1.64 (m, 4H), 1.55-1.38 (m, 2H), 1.32-1.12 (m, 2H), 0.94 (d, 3H).

Example 6b (9S,12S)-12-[(R)-1-Hydroxy-2-((R/S)-6-isopropyl-2,2-dimethyl-chroman-4-ylamino)-ethyl]-9-methyl-7,7-dioxo-2-oxa-7lambda*6*-thia-11-aza-bicyclo[12.3.1]octa-deca-1(18),14,16-trien-10-one Rf (DCM/MeOH/NH$_3$=95/4.5/0.5): 0.33.
MS (ES+): 587=[M+H]$^+$.

Example 6c (9S,12S)-12-[(R)-2-((R/S)-6-Bromo-chroman-4-ylamino)-1-hydroxy-ethyl]-9-methyl-7,7-dioxo-2-oxa-7lambda*6*-thia-11-aza-bicyclo[12.3.1]octadeca-1(18),14,16-trien-10-one Rf (DCM/MeOH/NH$_3$=95/4.5/0.5): 0.26.
MS (ES+): 595/597=[M+H]$^+$.
$^1$H-NMR (400 MHz, DMSO-d$_6$, 2 diastereomers): 8.20 (d, 0.5H), 8.10 (d, 0.5H), 7.77 (s, 0.5H), 7.70 (s, 0.5H), 7.48-7.38 (m, 1H), 7.17 (t, 1H), 6.79-6.71 (m, 4H), 5.92 (d, 0.5H), 5.81 (d, 0.5H), 4.66-4.52 (m, 1H), 4.37-4.05 (m, 4H), 3.97-3.83 (m, 1H), 3.80-3.6 (m, 1H), 3.25-3.01 (m, 3H), 3.00-2.76 (m, 4H), 2.71-2.62 (m, 1H), 2.54-2.43 (m, 1H), 2.38-2.13 (m, 2H), 1.84-1.65 (m, 4H), 1.12 (d, 1.5H), 1.02 (d, 1.5H).

Example 7

(10R,13S)-13-[(R)-1-Hydroxy-2-(3-isopropyl-benzylamino)-ethyl]-10-methyl-2-oxa-7,12-diaza-bicyclo[13.3.1]nonadeca-1(19),15,17-triene-8,11-dione The title compound can be prepared by an analogous reaction sequence as described for example 1, starting from [(1S,2S)-1-(3-allyloxy-benzyl)-3-chloro-2-hydroxy-propyl]-carbamic acid tert-butyl ester (building block B1) and using (R)—N-allyl-2-methyl-succinamic acid (building block A5) in step b) instead of BOC-N-methyl-(L)-alanine, followed by ring-closing metathesis and subsequent reaction steps.
MS (ES+): 496=[M+H]$^+$.
$^1$H-NMR (400 MHz, DMSO-d$_6$): 7.64 (d, 1H), 7.58 (q, 1H), 7.21-7.14 (m, 2H), 7.11-7.04 (m, 3H), 6.73-6.68 (m, 2H), 6.65-6.60 (m, 1H), 4.82 (br s, 1H), 4.04-3.88 (m, 3H), 3.73-3.61 (m, 2H), 3.43-3.35 (m, 2H), 3.04 (d, 1H), 2.89-2.80 (m, 1H), 2.79-2.70 (m, 1H), 2.68-2.59 (m, 1H), 2.58-2.40 (m, 2H), 2.22 (dd, 1H), 1.77-1.57 (m, 4H), 1.46-1.34 (m, 1H), 1.19 (d, 6H), 0.89 (d, 3H).

The following compounds 7a and 7b can be prepared by an analogous reaction sequence as described for example 7, starting from [(1S,2S)-1-(3-allyloxy-benzyl)-3-chloro-2-hydroxy-propyl]-carbamic acid tert-butyl ester (building block B1) and using in the final step instead of 3-isopropyl-benzylamine either 3-tert-butyl-benzylamine (building block C1) or 1-(3-tert-butyl-phenyl)-cyclopropylamine (building block C4).

Example 7a (10R,13S)-13-[(R)-2-(3-tert-Butyl-benzylamino)-1-hydroxy-ethyl]-10-methyl-2-oxa-7,12-diaza-bicyclo[13.3.1]nonadeca-1(19),15,17-triene-8,11-dione MS (ES+): 510=[M+H]$^+$.
$^1$H-NMR (400 MHz, DMSO-d$_6$): 7.64 (d, 1H), 7.58 (q, 1H), 7.31 (s, 1H), 7.24-7.17 (m, 2H), 7.11-7.05 (m, 2H), 6.74-6.67 (m, 2H), 6.65-6.61 (m, 1H), 4.82 (brs, 1H), 4.03-3.88 (m, 3H), 3.66 (d, 2H), 3.43-3.34 (m, 2H), 3.04 (d, 1H), 2.79-2.70 (m, 1H), 2.68-2.60 (m, 1H), 2.59-2.41 (m, 2H), 2.22 (dd, 1H), 1.77-1.57 (m, 4H), 1.45-1.36 (m, 1H), 1.27 (s, 9H), 0.89 (d, 3H).

Example 7b (10R,13S)-13-{(R)-2-[1-(3-tert-Butyl-phenyl)-cyclopropylamino]-1-hydroxy-ethyl}-10-methyl-2-oxa-7,12-diaza-bicyclo[13.3.1]nonadeca-1(19),15,17-triene-8,11-dione Rf (DCM/MeOH/NH$_3$=90/9/1): 0.33.
MS (ES+): 536=[M+H]$^+$.
$^1$H-NMR (400 MHz, DMSO-d$_6$): 7.63-7.55 (m, 2H), 7.31 (s, 1H), 7.19-7.13 (m, 2H), 7.07 (t, 1H), 7.03-6.99 (m, 1H), 6.72-6.66 (m, 2H), 6.64-6.60 (m, 1H), 4.68 (d, 1H), 4.02-3.84 (m, 3H), 3.40-3.33 (m, 1H), 3.05-2.98 (m, 1H), 2.78-2.70 (m, 1H), 2.68-2.59 (m, 1H), 2.56-2.52 (m, 1H), 2.44-2.36 (m, 1H), 2.22 (dd, 1H), 1.76-1.55 (m, 5H), 1.45-1.34 (m, 1H), 1.27 (s, 9H), 0.94-0.80 (m, 7H).

The starting materials can be prepared as described hereafter.

Non-natural amino acids can be prepared by methods disclosed in the literature and known to those skilled in the art (see, for example, *Tetrahedron* 2002, 58, 6951-6963, or *J. Am. Chem. Soc.* 1993, 115, 10125-10138).

Building block A1: (S)-3-(3-Benzyloxy-phenyl)-2-tert-butoxycarbonylamino-propionic acid methyl ester m. p.: 80-81° C.
$[\alpha]_D^{22}$: +39.1° (c=1.29, CHCl$_3$).
Rf (DCM/EtOAc=90/10): 0.69.
MS (ES+): 408=[M+Na]$^+$.
$^1$H-NMR (400 MHz, DMSO-d$_6$): 7.45-7.29 (m, 5H), 7.27 (d, 1H), 7.18 (t, 1H), 6.89 (s, 1H), 6.87-6.81 (m, 1H), 6.79 (d, 1H), 5.06 (s, 2H), 4.21-4.14 (m, 1H), 3.60 (s, 3H), 2.99-2.92 (m, 1H), 2.84-2.77 (m, 1H), 1.33 (s, 9H).

Building block A2: (S)-3-(3-Bromo-phenyl)-2-tert-butoxycarbonylamino-propionic acid methyl ester m. p.: 60-61° C.
$[\alpha]_D^{22}$: +50.8° (c=1.00, CHCl$_3$).
Rf (DCM/EtOAc=90/10): 0.54.
MS (ES+): 380=[M+Na]$^+$.
$^1$H-NMR (400 MHz, DMSO-d$_6$): 7.44 (s, 1H), 7.41-7.36 (m, 1H), 7.30 (d, 1H), 7.23 (d, 2H), 4.23-4.15 (m, 1H), 3.62 (s, 3H), 3.04-2.98 (m, 1H), 2.87-2.79 (m, 1H), 1.32 (s, 9H).

Building block A3: (S)-2-(tert-Butoxycarbonyl-cyclopropyl-amino)-propionic acid

To a solution of 1.5 ml (21.5 mmol, 3.85 eq) of cyclopropylamine in 1 ml of water are added 0.5 ml (5.57 mmol, 1 eq) of (+)-2-bromo-propionic acid. 2 ml of saturated sodium bicarbonate are added after 2 h, and the reaction mixture is stirred for 48 h and then concentrated. The residue is dissolved in 5 ml of 1 N sodium hydroxide and 5 ml of THF. 1.00 g (4.58 mmol, 0.82 eq) of (BOC)$_2$O is added, and the reaction mixture is stirred for 48 h and then acidified with 1 N HCl, until the pH is acidic. The organic layer is separated, washed with 1 N HCl and brine, dried over sodium sulfate, filtered and concentrated. The residue is purified by column chromatography on silica gel (CH$_2$Cl$_2$/MeOH/TFA/H$_2$O 90/10/0.5/1) to give the product.
MS (ES−): 228=[M−H]$^-$.
$^1$H-NMR (400 MHz, CDCl$_3$): 4.80-4.60 (br s, 1H), 2.60-2.40 (br s, 1H), 1.60-1.40 (m, 12H), 0.80-0.60 (m, 2H), 0.60-0.40 (m, 2H).

Building block A4: (S)-2-methyl-3-(prop-2-en-1-ylsulfonyl)-propionic acid a) (S)-3-Allylsulfanyl-2-methyl-propionic acid To a solution of 8.11 g (50 mmol) of (S)-3-acetylsulfanyl-2-methyl-propionic acid and 4.23 ml (50 mmol) of allyl bromide in 80 ml of MeOH are added dropwise at 0° C. 37.5 ml (150 mmol) of 4 N sodium hydroxide. The reaction mixture is stirred for 2 h at rt, then at 0° C. acidified with 165 ml (165 mmol) of 1 N HCl and extracted with EtOAc (2×165 ml). The combined organic phases are washed with 150 ml of saturated aq. sodium chloride and 150 ml of water, dried over sodium sulfate and concentrated to give the product in the form of a colorless oil.
Rf (DCM/MeOH=95/5): 0.50.
MS (LC/MS): 142.9=[M−H$_2$O+H]$^+$, 160.9=[M+H]$^+$.

b) (S)-2-methyl-3-(prop-2-en-1-ylsulfonyl)-propionic acid

To a solution of 8.7 g (50 mmol) of (S)-3-allylsulfanyl-2-methyl-propionic acid in 160 ml of acetonitrile and 40 ml of water are added at 0° C. 20.2 g (65 mmol) of OXONE® (potassium peroxymonosulfate). The mixture is stirred at rt for 17 h. Then additional 10.1 g (32.5 mmol) of OXONE® (potassium peroxymonosulfate) and after further 2 h additional 20.2 g (65 mmol) of OXONE® (potassium peroxymonosulfate) are added. Afterwards, stirring is continued for 3 h. The mixture is diluted with 400 ml of water and extracted with EtOAc (2×200 ml). The combined organic phases are washed with 200 ml of water, dried over sodium sulfate and concentrated to give the product in the form of a colorless oil.
Rf (DCM/MeOH=95/5): 0.37.
MS (LC/MS): 214.9=[M+Na]$^+$.

Building block A5: (R)—N-Allyl-2-methyl-succinamic acid a) (R)-2-Methyl-succinic acid 1-tert-butylester 4-methyl ester To a solution of 1.46 g (10 mmol) of (R)-2-methyl-succinic acid 4-methyl ester and 4.5 g (20 mmol) of (BOC)$_2$O in 20 ml of tBuOH are added 367 mg (3 mmol) of DMAP. The mixture is stirred for 1 h at rt, the solvent is removed under reduced pressure, and the residue is taken up in 50 ml of DCM. The mixture is extracted with 0.5 M HCl (3×30 ml), dried over sodium sulfate and concentrated to give the product in the form of a colorless oil.
MS (ES+): 203.2=[M+H]$^+$.
$^1$H-NMR (400 MHz, CDCl$_3$): 3.70 (s, 3H), 2.87-2.78 (m, 1H), 2.69 (dd, 1H), 2.37 (dd, 1H), 1.46 (s, 9H), 1.20 (d, 3H).

b) (R)-2-Methyl-succinic acid 1-tert-butyl ester

To a solution of 2.55 g (9.89 mmol) of (R)-2-methyl-succinic acid 1-tert-butylester 4-methyl ester in 20 ml of THF/MeOH (1/1) are added at 0° C. 10 ml (20 mmol) of 2 M sodium hydroxide. The mixture is stirred for 4 h at 0° C. and then acidified to pH 2-3 by addition of 1 M HCl. The organic solvents are evaporated. The residual aq. solution is extracted with DCM (3×30 ml), and the combined organic layers are dried over sodium sulfate and concentrated to give the product in the form of a colorless oil.
MS (ES+): 189.2=[M+H]$^+$.
$^1$H-NMR (400 MHz, CDCl$_3$): 2.86-2.78 (m, 1H), 2.73 (dd, 1H), 2.43 (dd, 1H), 1.46 (s, 9H), 1.22 (d, 3H).

c) (R)—N-Allyl-2-methyl-succinamic acid tert-butyl ester

To a stirred solution of 1.75 g (9.3 mmol) of (R)-2-methyl-succinic acid 1-tert-butyl ester, 2.01 g (13.0 mmol) of HOBt and 0.78 ml (10.2 mmol) of allylamine in 50 ml of DCM at 0° C. are added 2.18 g (11.2 mmol) of EDC.HCl. The mixture is allowed to warm to rt, and stirring is continued for 16 h. 8 ml of EtOH are added, and the mixture is washed with 0.5 M sodium carbonate (2×30 ml), 0.5 M HCl (2×30 ml) and water (30 ml), dried over sodium sulfate and evaporated to give the product in the form of an oil.
Rf (DCM/MeOH=95/5): 0.69.
MS (ES+): 228.2=[M+H]$^+$.
$^1$H-NMR (400 MHz, CDCl$_3$/CD$_3$OD {10/1}): 5.89-5.79 (m, 1H), 5.77 (br s, 1H), 5.23-5.12 (m, 2H), 3.91-3.87 (m, 2H), 2.94-2.85 (m, 1H), 2.57 (dd, 1H), 2.23 (dd, 1H), 1.46 (s, 9H), 1.21 (d, 3H).

d) (R)—N-Allyl-2-methyl-succinamic acid

To a solution of 1.98 g (8.7 mmol) of (R)—N-allyl-2-methyl-succinamic acid tert-butyl ester in 30 ml of DCM are added 3.57 ml (21.8 mmol) of triethylsilane and 8.76 ml (113 mmol) of TFA, and the mixture is stirred for 3 h and then concentrated by co-evaporation with toluene (3×30 ml) to give the solid product.
MS (ES+): 172.0=[M+H]$^+$.

$^1$H-NMR (400 MHz, CDCl$_3$): 5.93 (br s, 1H), 5.89-5.79 (m, 1H), 5.25-5.17 (m, 2H), 4.70 (br, s, 1H), 3.94-3.91 (m, 2H), 3.06-2.97 (m, 1H), 2.65 (dd, 1H), 2.41 (dd, 1H), 1.29 (d, 3H).

Building block B1: [(1S,2S)-1-(3-Allyloxy-benzyl)-3-chloro-2-hydroxy-propyl]-carbamic acid tert-butyl ester a) (S)-2-tert-Butoxycarbonylamino-3-(3-hydroxy-phenyl)-propionic acid methyl ester A solution of 5.81 g (15 mmol) of (S)-3-(3-benzyloxy-phenyl)-2-tert-butoxycarbonylamino-propionic acid methyl ester (building block A1) in 150 ml of EtOH is stirred at rt under a hydrogen atmosphere for 2 h in the presence of 1.5 g of 10% Pd/C. The catalyst is filtered off, and the filtrate is evaporated to give the product in the form of a colorless solid.
m.p.: 61-65° C.
Rf (DCM/EtOAc=80/20): 0.34.
MS (ES+): 318=[M+Na]$^+$.
$^1$H-NMR (400 MHz, DMSO-d$_6$): 9.27 (s, 1H), 7.22 (d, 1H), 7.04 (t, 1H), 6.63-6.56 (m, 3H), 4.15-4.07 (m, 1H), 3.60 (s, 3H), 2.91-2.84 (m, 1H), 2.79-2.71 (m, 1H), 1.33 (s, 9H).

b) (S)-3-(3-Allyloxy-phenyl)-2-tert-butoxycarbonylamino-propionic acid methyl ester To a solution of 2.34 g (7.5 mmol) of (S)-2-tert-butoxycarbonylamino-3-(3-hydroxy-phenyl)-propionic acid methyl ester in 15 ml of acetone are added 1.25 g (9.75 mmol) of powdered K$_2$CO$_3$ and 0.76 ml (9 mmol) of allyl bromide, and the mixture is stirred for 16 h at 80° C. 15 ml of water are added, and the mixture is extracted with DCM (2×15 ml). The combined organic layers are washed with 7.5 ml of 1 M sodium hydroxide and 7.5 ml of halfsaturated sodium chloride, dried over sodium sulfate and evaporated to give the product in the form of a colorless solid.
m. p.: 50-51° C.
[α]$_D^{22}$: +40.9° (c=1.18, CHCl$_3$).
Rf (DCM/EtOAc=80/20): 0.70.
MS (ES+): 358=[M+Na]$^+$.
$^1$H-NMR (400 MHz, DMSO-d$_6$): 7.25 (d, 1H), 7.17 (t, 1H), 6.83-6.75 (m, 3H), 6.08-5.97 (m, 1H), 5.40-5.34 (m, 1H), 5.26-5.21 (m, 1H), 4.52 (d, 2H), 4.19-4.12 (m, 1H), 3.61 (s, 3H), 2.98-2.92 (m, 1H), 2.84-2.77 (m, 1H), 1.33 (s, 9H).

c) [(S)-1-(3-Allyloxy-benzyl)-3-chloro-2-oxo-propyl]-carbamic acid tert-butyl ester A solution of 2.43 g (7.24 mmol) of (S)-3-(3-allyloxy-phenyl)-2-tert-butoxycarbonylamino-propionic acid methyl ester in 72 ml of THF is cooled to −78° C., and 2.1 ml (29 mmol) of chloroiodomethane are added. A 1.43 M THF solution of LDA (25.2 ml, 36.2 mmol) is added dropwise, while the temperature of the reaction mixture is maintained below −75° C. The mixture is stirred for an additional 30 min and then carefully quenched with 10.8 ml (188 mmol) of glacial acetic acid, while the temperature is maintained below −65° C. After stirring for 15 min at −78° C., the mixture is allowed to warm to 0° C., and 110 ml of half-saturated aq. sodium chloride solution are added. The mixture is extracted with TBME (2×110 ml), and the combined organic layers are washed with 110 ml of 1 M sodium sulfite and 110 ml of water, dried over sodium sulfate and evaporated to give the product.
Rf (cyclohexane/EtOAc=50/50): 0.55.
MS (LC/MS): 375.8=[M+Na]$^+$.

d) [(1S,2S)-1-(3-Allyloxy-benzyl)-3-chloro-2-hydroxy-propyl]-carbamic acid tert-butyl ester A stirred solution of 568 mg (14.5 mmol) of sodium borohydride in 43 ml of EtOH is cooled to −78° C., and a solution of 4.36 g (7.24 mmol) of [(S)-1-(3-allyloxy-benzyl)-3-chloro-2-oxo-propyl]-carbamic acid tert-butyl ester in 145 ml of EtOH is added dropwise, while maintaining the temperature of the mixture below −70° C. At −78° C. stirring is continued for 30 min, then 36.8 ml of 1 M HCl are added dropwise, and the mixture is allowed to warm to rt. The EtOH is evaporated, and the residual aq. solution is extracted with EtOAc (2×72 ml). The combined organic layers are washed with 36 ml of water, dried over sodium sulfate and evaporated. The residue is purified by chromatography on silica gel (cyclohexane/EtOAc 90/10 to 50/50) to give the product in the form of a pale brown solid.
m. p.: 140-143° C.
[α]$_D^{22}$: −12.3° (c=1.02, CHCl$_3$).
Rf (cyclohexane/EtOAc=50/50): 0.43.
MS (ES−): 354=[M−H]$^-$.
$^1$H-NMR (400 MHz, DMSO-d$_6$): 7.13 (t, 1H), 6.79-6.70 (m, 3H), 6.68 (d, 1H), 6.08-5.97 (m, 1H), 5.42-5.34 (m, 2H), 5.23 (d, 1H), 4.50 (d, 2H), 3.68-3.63 (m, 1H), 3.61-3.52 (m, 2H), 3.50-3.44 (m, 1H), 2.98-2.92 (m, 1H), 1.28 (s, 9H).

Building block B2: [(1S,2S)-1-(3-Allyl-benzyl)-3-chloro-2-hydroxy-propyl]-carbamic acid tert-butyl ester a) (S)-3-(3-Allyl-phenyl)-2-tert-butoxycarbonylamino-propionic acid methyl ester A solution of 4.21 g (11.75 mmol) of (S)-3-(3-bromo-phenyl)-2-tert-butoxycarbonylamino-propionic acid methyl ester (building block A2), 5.58 ml (17.6 mmol) of allyltributyltin and 1.51 g (35.3. mmol) of lithium chloride in 118 ml of dimethylamide is degassed. Under an argon atmosphere 367 mg (0.59 mmol) of SK-CC02-A are added, and the mixture is stirred at 100° C. for 17 h. After addition of 41 ml of saturated potassium fluoride solution at 0° C., the mixture is stirred at rt for 30 min, the resulting suspension is filtered and washed with EtOAc (3×59 ml), and the layers of the filtrate are separated. The aq. phase is extracted with 179 ml of EtOAc, and the combined organic layers are washed with water, dried over sodium sulfate and evaporated. The residue is purified by chromatography on silica gel (cyclo-hexane/EtOAc 90/10) to give the product in the form of a yellow oil.
Rf (cyclohexane/EtOAc=80/20): 0.31.
MS (ES+): 342.1=[M+Na]$^+$.
$^1$H-NMR (400 MHz, DMSO-d$_6$): 7.26 (d, 1H), 7.19 (t, 1H), 7.06-6.99 (m, 3H), 5.98-5.87 (m, 1H), 5.18-5.00 (m, 2H), 4.18-4.10 (m, 1H), 3.59 (s, 3H), 3.32 (d, 2H), 2.98-2.91 (m, 1H), 2.87-2.79 (m, 1H), 1.32 (s, 9H).

b) [(S)-1-(3-Allyl-benzyl)-3-chloro-2-oxo-propyl]-carbamic acid tert-butyl ester A solution of 1.95 g (6.1 mmol) of (S)-3-(3-allyl-phenyl)-2-tert-butoxycarbonylamino-propionic acid methyl ester in 61 ml of THF is cooled to −78° C., and 1.8 ml (24.4 mmol) of chloro-iodomethane are added. A 1.47 M THF solution of LDA (20.8 ml, 30.5 mmol) is added dropwise, while the temperature of the reaction mixture is maintained below −73° C. The mixture is stirred for an additional 30 min and then carefully quenched with 9.1 ml (159 mmol) of glacial acetic acid, while the temperature is maintained below −65° C. After stirring for 15 min at −78° C., the mixture is allowed to warm to 0° C., and 92 ml of a half-saturated aq. sodium chloride solution are added. The mixture is extracted with TBME (2×92 ml), and the combined organic layers are washed with 92 ml of 1 M sodium sulfite and 92 ml of water, dried over sodium sulfate and evaporated to give the product.

Rf (cyclohexane/EtOAc=80/20): 0.34.
MS (LC/MS): 359.8=[M+Na]$^+$.

c) [(1S,2S)-1-(3-Allyl-benzyl)-3-chloro-2-hydroxy-propyl]-carbamic acid tert-butyl ester A stirred solution of 471 mg (12.2 mmol) of sodium borohydride in 44 ml of EtOH is cooled to −78° C., and a solution of 3.2 g (6.1 mmol) of [(S)-1-(3-allyl-benzyl)-3-chloro-2-oxo-propyl]-carbamic acid tert-butyl ester in 90 ml of EtOH is added dropwise, while maintaining the temperature of the reaction mixture below −75° C. At −78° C., stirring is continued for 1 h. The mixture is then allowed to warm to rt within 17 h. At −78° C., 31 ml of 1 M HCl are added dropwise, and the mixture is allowed to warm to rt. The EtOH is evaporated, and the residual aq. solution is extracted with EtOAc (2×61 ml). The combined organic layers are washed with 61 ml of half-saturated sodium chloride solution, dried over sodium sulfate and evaporated. The residue is purified by chromatography on silica gel (cyclohexane/EtOAc 90/10 to 80/20) to give the product in the form of a pale brown solid.

m. p.: 123-126° C.
Rf (cyclohexane/EtOAc=80/20): 0.19.
MS (ES+): 362.2=[M+H]$^+$.
$^1$H-NMR (400 MHz, DMSO-d$_6$): 7.15 (t, 1H), 7.04-6.94 (m, 3H), 6.67 (d, 1H), 5.97-5.87 (m, 1H), 5.40 (d, 1H), 5.09-4.99 (m, 2H), 3.68-3.52 (m, 3H), 3.49-3.43 (m, 1H), 3.00-2.94 (m, 1H), 2.58-2.52 (m, 1H), 1.28 (s, 9H).

Building block C1: 3-tert-Butyl-benzylamine a) Trifluoromethanesulfonic acid 3-tert-butyl-phenyl ester To an ice-cold solution of 10.0 g (65 mmol) of 3-tert-butylphenol in 50 ml of pyridine are added slowly 33.3 ml (198 mmol) of Tf$_2$O. After stirring overnight at rt, the mixture is poured onto ice-water (800 ml) and extracted with Et$_2$O. After drying the organic phase over magnesium sulfate, the solvent is removed in vacuo, and the residue is purified by chromatography on silica gel (hexane/EtOAc 95/5) to give the product in the form of a a colorless oil.

HPLC (Nucleosil 100-3 C18HD, 4×70 mm, 3 µm, 1.0 ml/min, 20-100% AcCN/H$_2$O/6 min, 100% AcCN/1.5 min, 100-20% AcCN/H$_2$O/0.5 min) retention time: 6.20 min.
Rf (hexane/EtOAc=95/5): 0.75.
$^1$H-NMR (400 MHz, CDCl$_3$): 7.44-7.39 (m, 2H), 7.24-7.23 (m, 1H), 7.11 (d, 1H), 1.38 (s, 9H).

b) 3-tert-Butyl-benzonitrile

A mixture of 2.0 g (7.1 mmol) of trifluoromethanesulfonic acid 3-tert-butyl-phenyl ester, 1.0 g (8.5 mmol) of zinc cyanide and 0.41 g (0.35 mmol) of Pd[P(C$_6$H$_5$)$_3$]$_4$ in 24 ml of DMF is degassed for 10 min in an ultrasonic bath and then heated overnight to 80° C. After cooling to rt, the reaction mixture is quenched with water and extracted with EtOAc. The organic phase is washed with brine, dried over sodium sulfate and evaporated in vacuo. The residue is purified by chromatography on silica gel (hexane/EtOAc 95/5) to give the product in the form of a yellow oil.

HPLC (Nucleosil 100-3 C18HD, 4×70 mm, 3 µm, 1.0 ml/min, 20-100% AcCN/H$_2$O/6 min, 100% AcCN/1.5 min, 100-20% AcCN/H$_2$O/0.5 min) retention time: 5.19 min.
Rf (hexane/EtOAc=95/5): 0.39.
$^1$H-NMR (400 MHz, CDCl$_3$): 7.70 (d, 1H), 7.63 (d, 1H), 7.50 (d, 1H), 7.41 (dd, 1H), 1.39 (s, 9H).

c) 3-tert-Butyl-benzylamine

A mixture of 0.84 g (5.1 mmol) of 3-tert-butyl-benzonitrile, 1 ml of 25% aq. NH$_3$ and 0.1 g of Raney-Nickel is hydrogenated at 40° C. After the completion of the reaction, the catalyst is filtered off and washed with MeOH. The filtrate is evaporated in vacuo, and the residue is purified by chromatography on silica gel (DCM/MeOH 90/10) to give the product in the form of a green oil.

HPLC (Nucleosil 100-3 C18HD, 4×70 mm, 3 µm, 1.0 ml/min, 20-100% AcCN/H$_2$O/6 min, 100% AcCN/1.5 min, 100-20% AcCN/H$_2$O/0.5 min) retention time: 2.81 min.
Rf (hexane/EtOAc=95/5): 0.26.
MS (ES+): 164=[M+H]$^+$.
$^1$H-NMR (400 MHz, CDCl$_3$): 7.40-7.33 (m, 3H), 7.20-7.18 (m, 1H), 3.90 (s, 2H), 1.60 (bs, 2H), 1.39 (s, 9H).

Building block C2:
C-(5-Cyclopropyl-pyridin-3-yl)-methylamine a) 5-Cyclopropyl-nicotinonitrile To a solution of 1.83 g (10 mmol) of 5-bromo-nicotinonitrile in 20 ml of dioxane are added 6.7 g (30 mmol) of potassium phosphate and 1.29 g (15 mmol) of cyclopropyl boronic acid. The mixture is degassed, and under an argon atmosphere 63 mg (0.1 mmol) of SK-CC02-A are added. The mixture is stirred at 100° C. for 17 h, diluted with 270 ml of water and extracted with Et$_2$O (2×270 ml). The combined organic layers are washed with 270 ml of water, dried over sodium sulfate and concentrated to give the product in the form of a brown oil.

Rf (DCM/MeOH=98/2): 0.52.
MS (LC/MS): 145.0=[M+H]$^+$.

b) C-(5-Cyclopropyl-pyridin-3-yl)-methylamine

To a solution of 2.33 g (10 mmol) of 5-cyclopropyl-nicotinonitrile in 100 ml of MeOH is added Raney-Nickel [washed with MeOH (3×20 ml)]. The mixture is stirred under a hydrogen atmosphere for 160 min. The catalyst is filtered off through Hyflo and washed with MeOH. The filtrate is evaporated in vacuo, and the residue is purified by chromatography on silica gel (DCM/MeOH 98/2 to 85/15 to DCM/MeOH/NH$_3$ 90/9/1) to give the product in the form of a green oil.

Rf (DCM/MeOH=90/10): 0.17.
MS (ES+): 149=[M+H]$^+$.
$^1$H-NMR (400 MHz, DMSO-d$_6$): 8.25 (d, 1H), 8.21 (d, 1H), 7.32 (t, 1H), 3.67 (s, 2H), 1.99 (br, 2H), 1.96-1.88 (m, 1H), 1.02-0.94 (m, 2H), 0.75-0.69 (m, 2H).

Building block C3:
1-(3-Bromo-phenyl)-cyclopropylamine

The title compound can be prepared as described by Bertus et al. (*J. Org. Chem.* 2003, 68, 7133-7136), starting from 3-bromo-benzonitrile.

HPLC (Nucleosil 100-3 C18HD, 4×70 mm, 3 µm, 1.0 ml/min, 5-100% AcCN/H$_2$O/6 min, 100% AcCN/1.5 min, 100-5% AcCN/H$_2$O/0.5 min) retention time: 3.36 min.

Rf (DCM/MeOH=90/10): 0.53.

MS (ES+): 213=[M]$^+$.

$^1$H-NMR (400 MHz, DMSO-d$_6$): 9.05 (br s, 3H, NH3), 7.64 (d, 1H), 7.52 (dd, 1H), 7.40 (dd, 1H), 7.35 (t, 1H), 1.42-1.38 (m, 2H), 1.23-1.19 (m, 2H).

Building block C4:
1-(3-tert-Butyl-phenyl)-cyclopropylamine

The title compound can be prepared as described by Bertus et al. (*J. Org. Chem.* 2003, 68, 7133-7136), starting from 3-tert-butyl-benzonitrile.

Rf (cyclohexane/EtOAc=50/50): 0.19.

MS (LC/MS): 190.1=[M+H]$^+$.

$^1$H-NMR (400 MHz, CDCl3): 7.40-7.38 (m, 1H), 7.27-7.26 (m, 2H), 7.15-7.12 (m, 1H), 1.91 (br s, 2H), 1.35 (s, 9H), 1.09-1.05 (m, 2H), 1.03-0.99 (m, 2H).

Building block C5:
(R/S)-6-Isopropyl-2,2-dimethyl-chroman-4-ylamine a) 6-Isopropyl-2,2-dimethyl-chroman-4-one To a solution of 3.5 g (20 mmol) of 1-(2-hydroxy-5-isopropyl-phenyl)-ethanone (commercially available from APIN) in 50 ml of toluene are added 2.2 ml (30 mmol) of acetone and 0.83 ml (10 mmol) of pyrrolidine, and the mixture is refluxed for 24 h using a Dean-Stark trap. After cooling to rt, the solvent is removed in vacuo, and the residue is purified by chromatography on silica gel (PE 40-60/EtOAc 25/1 to 10/1) to give the product in the form of a brown oil.

HPLC (Nucleosil 100-3 C18HD, 4×70 mm, 3 µm, 1.0 ml/min, 20-100% AcCN/H$_2$O/6 min, 100% AcCN/1.5 min, 100-20% AcCN/H$_2$O/0.5 min) retention time: 5.54 min.

Rf (PE 40-60/EtOAc=20/1): 0.13.

MS (ES+): 219=[M–H]$^+$.

$^1$H-NMR (300 MHz, CDCl$_3$): 7.70 (d, 1H), 7.35 (dd, 1H), 6.82 (d, 1H), 2.83 (hept, 1H), 1.42 (s, 6H), 1.2 (d, 6H).

b) (R/S)-6-Isopropyl-2,2-dimethyl-chroman-4-one oxime

A mixture of 2.2 g (10 mmol) of 6-isopropyl-2,2-dimethyl-chroman-4-one, 2.1 g (30 mmol) of hydroxylamine hydrochloride and 6.9 g (50 mmol) of potassium carbonate in 30 ml of EtOH is refluxed for 18 h. The solvent is removed in vacuo, and the residue is taken up in water (30 ml). The aq. mixture is extracted with DCM, and the organic phase is dried over sodium sulfate and evaporated to give the product in the form of a brown oil, which solidifies after a while.

HPLC (Nucleosil 100-3 C18HD, 4×70 mm, 3 µm, 1.0 ml/min, 20-100% AcCN/H$_2$O/6 min, 100% AcCN/1.5 min, 100-20% AcCN/H$_2$O/0.5 min) retention time: 5.24 min.

Rf (DCM/MeOH=20/1): 0.44.

MS (ES+): 235=[M]$^+$.

c)
(R/S)-6-Isopropyl-2,2-dimethyl-chroman-4-ylamine

A solution of 2.4 g (10 mmol) of (R/S)-6-isopropyl-2,2-dimethyl-chroman-4-one oxime in 50 ml of MeOH is hydrogenated in the presence of 1.1 ml of conc. HCl using 240 mg of Pd/C (10%). After the completion of the reaction, the catalyst is filtered off and washed with MeOH. The filtrate is evaporated in vacuo, and the residue is taken up in DCM. The DCM phase is washed with aq. potassium carbonate, dried over sodium sulfate, filtered and evaporated in vacuo to give the product.

HPLC (Nucleosil 100-3 C18HD, 4×70 mm, 3 µm, 1.0 ml/min, 20-100% AcCN/H$_2$O/6 min, 100% AcCN/1.5 min, 100-20% AcCN/H$_2$O/0.5 min) retention time: 3.24 min.

Rf (DCM/MeOH=90/10): 0.39.

MS (ES+): 222=[M–H]$^+$.

Building block C6:
(R/S)-6-Bromo-chroman-4-ylamine

To a solution of 1.0 g (4.4 mmol) of 6-bromo-chroman-4-one (commercially available from SPECS) in 30 ml of MeOH are added 6.7 g (88 mmol) of ammonium acetate. After stirring for 15 min at rt, 0.83 g (13.2 mmol) of sodium cyanoborohydride are added, and the mixture is refluxed for 15 h. After cooling to rt, the mixture is acidified with 6 N HCl and extracted with Et$_2$O. The aq. phase is adjusted to pH 10 with 2 N sodium hydroxide and extracted with DCM. The DCM phase is dried over magnesium sulfate and evaporated. The residue is purified by chromatography on silica gel (DCM/MeOH 95/5 to 90/10) to give the product in the form of a colorless oil.

HPLC (Nucleosil 100-3 C18HD, 4×70 mm, 3 µm, 1.0 ml/min, 5-100% AcCN/H$_2$O/6 min, 100% AcCN/1.5 min, 100-5% AcCN/H$_2$O/0.5 min) retention time: 3.24 min.

MS (ES+): 212=[M–NH$_2$]$^+$.

$^1$H-NMR (400 MHz, CDCl$_3$): 7.47 (s, 1H), 7.23 (d, 1H), 6.65 (d, 1H), 4.38-4.20 (m, 2H), 4.03 (t, 1H), 2.21-2.10 (m, 1H), 1.90-1.80 (m, 1H), 1.60 (brs, 2H).

Building block C7:
(S)-6-Isopropyl-2,2-dimethyl-chroman-4-ylamine a) (R)-6-Isopropyl-2,2-dimethyl-chroman-4-ol A suspension of 4.18 g (19 mmol) of 6-isopropyl-2,2-dimethyl-chroman-4-one and 250 mg of molecular sieve (4 Å) in 85 ml of abs. THF is stirred for 2 h at rt under an argon atmosphere. 1.9 ml (1.9 mmol) of (S)-tetrahydro-1-methyl-3,3-diphenyl-1H,3H-pyrrolo(1,2-C)-(1,3,2)oxazaborole (1 M in toluene; FLUKA) are then added. After cooling to −25° C., 7.1 ml (14.2 mmol) of BH$_3$—SMe$_2$ (2 M in THF) are added over a period of 20 min. The mixture is stirred for 1 h and then quenched by addition of MeOH (20 ml). The solvent is removed in vacuo, and the residue is purified by chromatography on silica gel (hexane/EtOAc 6/1) to give the product in the form of a yellow oil.

HPLC (Nucleosil 100-3 C18HD, 4×70 mm, 3 µm, 1.0 ml/min, 20-100% AcCN/H$_2$O/6 min, 100% AcCN/1.5 min, 100-20% AcCN/H$_2$O/0.5 min) retention time: 4.63 min.

Rf (hexane/EtOAc=4/1): 0.33.

MS (ES+): 203=[M–OH]$^+$.

$^1$H-NMR (300 MHz, CDCl$_3$): 7.30 (d, 1H), 7.04 (dd, 1H), 6.72 (d, 1H), 4.84 (dd, 1H), 2.86 (hept, 1H), 2.18 (dd, 1H), 1.87 (dd, 1H), 1.6 (d, 1H), 1.44 (s, 3H), 1.32 (s, 3H), 1.23 (d, 6H).

The enantiomeric excess is determined by chiral HPLC (Chiralpak AD-H, 4.6×250 mm, 5 µm, 0.5 ml/min, hexane/EtOH=95/5): 96% ee, retention time=12.2 min (minor) and 13.4 min (major).

b) (S)-4-Azido-6-isopropyl-2,2-dimethyl-chroman

To a stirred ice-cold solution of 4.1 g (18 mmol) of (R)-6-isopropyl-2,2-dimethyl-chroman-4-ol and 6.56 g (21 mmol)

of DPPA in 20 ml of toluene is added over a period of 20 min a solution of 3.30 g (21 mmol) of DBU in toluene (30 ml). Stirring is continued for 15 h at rt.

The solvent is removed in vacuo, and the residue is purified by chromatography on silica gel (hexane/EtOAc 6/1) to give the product in the form of a pale yellow oil.

HPLC (Nucleosil 100-3 C18HD, 4×70 mm, 3 μm, 1.0 ml/min, 20-100% AcCN/H$_2$O/6 min, 100% AcCN/1.5 min, 100-20% AcCN/H$_2$O/0.5 min) retention time: 6.15 min.

Rf (hexane/EtOAc=4/1): 0.50.

MS (ES+): 203=[M−N$_3$]$^+$.

$^1$H-NMR (300 MHz, CDCl$_3$): 7.17 (d, 1H), 7.06 (dd, 1H), 6.74 (d, 1H), 4.58 (dd, 1H), 2.86 (hept, 1H), 2.16 (dd, 1H), 1.99 (dd, 1H), 1.44 (s, 3H), 1.33 (s, 3H), 1.24 (d, 6H).

c) (S)-6-Isopropyl-2,2-dimethyl-chroman-4-ylamine

A solution of 2.0 g (7.5 mmol) of (S)-4-azido-6-isopropyl-2,2-dimethyl-chroman in 50 ml of MeOH is hydrogenated using 500 mg of Pd/C (10%). After the completion of the reaction, the catalyst is filtered off and washed with MeOH. The filtrate is evaporated in vacuo, and the residue is purified by chromatography on silica gel (DCM/MeOH 95/5) to give the product in the form of a pale yellow oil.

HPLC (Nucleosil 100-3 C18HD, 4×70 mm, 3 μm, 1.0 ml/min, 20-100% AcCN/H$_2$O/6 min, 100% AcCN/1.5 min, 100-20% AcCN/H$_2$O/0.5 min) retention time: 3.16 min.

Rf (DCM/MeOH=9/1): 0.33.

MS (ES+): 203=[M−NH2]$^+$.

$^1$H-NMR (300 MHz, CDCl$_3$): 7.28 (d, 1H), 7.0 (dd, 1H), 6.71 (d, 1H), 4.0 (dd, 1H), 2.86 (hept, 1H), 2.07 (dd, 1H), 1.66 (dd, 1H), 1.57 (s, 2H, NH2), 1.42 (s, 3H), 1.28 (s, 3H), 1.23 (d, 6H).

The enantiomeric excess is determined by chiral HPLC (Chiralpak AD-H, 4.6×250 mm, 5 μm, 1 ml/min, hexane/EtOH=98/2+0.1% Et$_3$N): 81% ee, retention time=7.71 min (major) and 9.40 min (minor).

Building block C8:
(R/S)-6-Bromo-2,2-dimethyl-chroman-4-ylamine

The title compound can be prepared by an analogous reaction sequence as described for building block C5.

HPLC (Nucleosil 100-3 C18HD, 4×70 mm, 3 μm, 1.0 ml/min, 20-100% AcCN/H$_2$O/6 min, 100% AcCN/1.5 min, 100-20% AcCN/H$_2$O/0.5 min) retention time: 2.59 min.

Rf (DCM/MeOH=9/1): 0.37.

MS (ES+): 240=[M−NH$_2$]$^+$.

The invention claimed is:

1. A compound of the formula

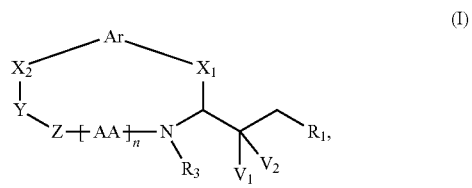

in which

R$_1$ is (CH$_2$)$_k$N(R$_a$)R$_b$, in which
  k is 0, 1 or 2; and either
  R$_a$ and R$_b$, independently, are hydrogen or an optionally substituted (C$_{1-8}$)alkyl, (C$_{3-7}$)cycloalkyl, (C$_{3-7}$)cycloalkyl(C$_{1-4}$)alkyl, aryl, aryl(C$_{1-4}$)alkyl, heteroaryl, heteroaryl-(C$_{1-4}$)alkyl, chroman-4-yl, isochroman-4-yl, thiochroman-4-yl, isothiochroman-4-yl, 1,1-dioxo-1lambda*6*-thiochroman-4-yl, 2,2-dioxo-2lambda*6*-isothiochroman-4-yl, 1,2,3,4-tetrahydroquinol-4-yl, 1,2,3,4-tetrahydroisoquinol-4-yl, 1,2,3,4-tetrahydronaphth-1-yl, 1,1-dioxo-1,2,3,4-tetrahydro-1lambda*6*-benzo[e][1,2]thiazin-4-yl, 2,2-dioxo-1,2,3,4-tetrahydro-2lambda*6*-benzo[c][1,2]thiazin-4-yl, 1,1-dioxo-3,4-dihydro-1H-1lambda*6*-benzo[c][1,2]oxathiin-4-yl, 2,2-dioxo-3,4-dihydro-2H-2lambda*6*-benzo[e][1,2]oxathiin-4-yl, 2,3,4,5-tetrahydrobenzo[b]oxepin-5-yl or 1,3,4,5-tetrahydrobenzo[c]oxepin-5-yl group or R$_a$ and R$_b$, together with the nitrogen, to which they are attached, form an optionally substituted pyrrolidinyl, 1-piperidinyl, 4-morpholinyl or piperazinyl group;
R$_3$ is hydrogen or (C$_{1-4}$)alkyl; either
V$_1$ is hydrogen and V$_2$ is hydroxyl; or
V$_1$ and V$_2$ together are oxo;
X$_1$ is (C$_{1-8}$)alkylene;
X$_2$ is (C$_{1-8}$)alkylene, O, S, C(=O), C(=O)O, OC(=O), C(=O)N(R$_2$)—(C$_{1-8}$)alkylenoxy attached via its carbonyl function to Y and attached via the oxygen atom of its alkylenoxy moiety to Ar, N(R$_2$)C(=O), C(=O)N(R$_2$) or N(R$_2$), in which R$_2$ is hydrogen or (C$_{1-4}$)alkyl;
Y is (C$_{1-10}$)alkylene, (C$_{1-8}$)alkylenoxy(C$_{1-6}$)alkylene, (C$_{1-10}$)alkenylene or (C$_{1-8}$)alkenylenoxy-(C$_{1-6}$)alkylene;
Ar is phenylene to which X$_1$ and X$_2$ are attached in meta or para position to each other; and either Z is C(=O), AA is N[(C$_{1-4}$)alkyl or (C$_{3-7}$)cycloalkyl]CH(CH$_3$)C(=O) and n is 1; or Z is S(=O)$_2$, AA is CH$_2$CH[(C$_{1-4}$)alkyl]C(=O), and n is 1, the number of ring atoms included in the macrocyclic ring being 14, 15, 16, 17 or 18, in free base form or in acid addition salt form.

2. The compound according to claim 1 of the formula I, in free base form or in pharmaceutically acceptable acid addition salt form, for use as a medicament.

3. The compound according to claim 1 of the formula I, in free base form or in pharmaceutically acceptable acid addition salt form, for use in the treatment of neurological or vascular disorders related to beta-amyloid generation and/or aggregation selected from Alzheimer's disease, Down's Syndrome, memory and cognitive impairment, dementia, amyloid neuropathies, brain inflammation, nerve and brain trauma, vascular amyloidosis, and cerebral hemorrhage with amyloidosis.

4. A pharmaceutical composition comprising a compound as claimed in claim 1 of the formula I, in free base form or in pharmaceutically acceptable acid addition salt form, as active ingredient and a pharmaceutical carrier or diluent.

5. The compound according to claim 1, in free base form or in acid addition salt form, which is selected from the group consisting of:

(10S,13S)-13-[(R)-1-Hydroxy-2-(3-isopropyl-benzylamino)-ethyl]-9,10-dimethyl-2-oxa-9,12-diaza-bicyclo[13.3.1]nonadeca-1(19),15,17-triene-8,11-dione;

(10S,13S)-13-((R)-2-Benzylamino-1-hydroxy-2-ethyl]-9,10-dimethyl-2-oxa-9,12-diaza-bicyclo[13.3.1]nonadeca-1(19),15,17-triene-8,11-dione;

(10S,13S)-13-{(R)-2-[1-(3-Bromo-phenyl)-cyclopropylamino]-1-hydroxy-ethyl}-9,10-dimethyl-2-oxa-9,12-diaza-bicyclo[13.3.1]nonadeca-1(19),15,17-triene-8,11-dione;

(10S,13S)-13-[(R)-1-Hydroxy-2-((R/S)-6-isopropyl-2,2-dimethyl-chroman-4-ylamino)-ethyl]-9,10-dimethyl-2-oxa-9,12-diaza-bicyclo[13.3.1]nonadeca-1(19),15,17-triene-8,11-dione;

(10S,13S)-13-[(R)-2-((R/S)-6-bromo-2,2-dimethyl-chroman-4-ylamino)-1-hydroxy-ethyl]-9,10-dimethyl-2-oxa-9,12-diaza-bicyclo[13.3.1]nonadeca-1(19),15,17-triene-8,11-dione;

(10S,13S)-13-[(R)-1-Hydroxy-2-((S)-6-isopropyl-2,2-dimethyl-chroman-4-ylamino)-ethyl]-9,10-dimethyl-2-oxa-9,12-diaza-bicyclo[13.3.1]nonadeca-1(19),15,17-triene-8,11-dione;

(12S,15S)-15-[(R)-1-Hydroxy-2-(3-isopropyl-benzylamino)-ethyl]-11,12-dimethyl-2-oxa-11,14-diaza-bicyclo[15.3.1]henicosa-1(21),17,19-triene-10,13-dione;

(11S,14S)-14-[(R)-1-Hydroxy-2-(3-isopropyl-benzylamino)-ethyl]-10,11-dimethyl-2-oxa-10,13-diaza-bicyclo[14.3.1]icosa-1(20),16,18-triene-9,12-dione;

(9S,12S)-12-[(R)-1-Hydroxy-2-(3-isopropyl-benzylamino)-ethyl]-8,9-dimethyl-2-oxa-8,11-diaza-bicyclo[12.3.1]octadeca-1(18),14,16-triene-7,10-dione;

(8S,11S)-11-[(R)-1-Hydroxy-2-(3-isopropyl-benzylamino)-ethyl]-7,8-dimethyl-2-oxa-7,10-diaza-bicyclo[11.3.1]heptadeca-1(17),13,15-triene-6,9-dione;

(10S,13S)-9-Cyclopropyl-13-[(R)-1-hydroxy-2-(3-isopropyl-benzylamino)-ethyl]-10-methyl-2-oxa-9,12-diaza-bicyclo[13.3.1]nonadeca-1(19),15,17-triene-8,11-dione;

(3S,6S)-3-[(R)-1-Hydroxy-2-(3-isopropyl-benzylamino)-ethyl]-6,7-dimethyl-4,7-diaza-bicyclo[13.3.1]nonadeca-1(18),15(19),16-triene-5,8-dione;

(3S,6S)-3-{(R)-2-[(5-cyclopropyl-pyridine-3-ylmethyl)-amino]-1-hydroxy-ethyl}-6,7-dimethyl-4,7-diaza-bicyclo[13.3.1]nonadeca-1(18),15(19),16-triene-5,8-dione;

(3S,6S)-3-[(R)-1-Hydroxy-2-(3-isopropyl-benzylamino)-ethyl]-6,7-dimethyl-4,7-diaza-bicyclo[12.3.1]octadeca-1(17),14(18),15-triene-5,8-dione;

(9S,12S)-12-[(R)-1-Hydroxy-2-(3-isopropyl-benzylamino)-ethyl]-9-methyl-7,7-dioxo-2-oxa-7lambda*6*-thia-11-aza-bicyclo[12.3.1]octadeca-1(18),14,16-trien-10-one;

(9S,12S)-12-{(R)-2-[1-(3-Bromo-phenyl)-cyclopropylamino]-1-hydroxy-ethyl}-9-methyl-7,7-dioxo-2-oxa-7lambda*6*-thia-11-aza-bicyclo[12.3.1]octadeca-1(18),14,16-trien-10-one;

(9S,12S)-12-[(R)-1-Hydroxy-2-((R/S)-6-isopropyl-2,2-dimethyl-chroman-4-ylamino)-ethyl]-9-methyl-7,7-dioxo-2-oxa-7lambda*6*-thia-11-aza-bicyclo[12.3.1]octa-deca-1(18),14,16-trien-10-one; and (9S,12S)-12-[(R)-2-((R/S)-6-Bromo-chroman-4-ylamino)-1-hydroxy-ethyl]-9-methyl-7,7-dioxo-2-oxa-7lambda*6*-thia-11-aza-bicyclo[12.3.1]octadeca-1(18),14,16-trien-10-one.

6. The compound according to claim 5 of the formula I, in free base form or in pharmaceutically acceptable acid addition salt form, for use as a medicament.

7. The compound according to claim 5 of the formula I, in free base form or in pharmaceutically acceptable acid addition salt form, for use in the treatment of neurological or vascular disorders related to beta-amyloid generation and/or aggregation selected from Alzheimer's disease, Down's Syndrome, memory and cognitive impairment, dementia, amyloid neuropathies, brain inflammation, nerve and brain trauma, vascular amyloidosis, and cerebral hemorrhage with amyloidosis.

8. A pharmaceutical composition comprising a compound as claimed in claim 5 of the formula I, in free base form or in pharmaceutically acceptable acid addition salt form, as active ingredient and a pharmaceutical carrier or diluent.

* * * * *